US011685720B2

(12) United States Patent
Dai et al.

(10) Patent No.: US 11,685,720 B2
(45) Date of Patent: Jun. 27, 2023

(54) SALT FORMS OF URAT-1 INHIBITORS

(71) Applicant: INVENTISBIO CO., LTD., Shanghai (CN)

(72) Inventors: Xing Dai, Short Hills, NJ (US); Yueheng Jiang, Belmont, MA (US)

(73) Assignee: INVENTISBIO CO., LTD., Shanghai (CN)

( * ) Notice: Subject to any disclaimer, the term of this patent is extended or adjusted under 35 U.S.C. 154(b) by 0 days.

(21) Appl. No.: 17/748,134

(22) Filed: May 19, 2022

(65) Prior Publication Data

US 2022/0371996 A1    Nov. 24, 2022

Related U.S. Application Data

(63) Continuation of application No. 17/041,855, filed as application No. PCT/CN2019/079619 on Mar. 26, 2019, now Pat. No. 11,339,127.

(30) Foreign Application Priority Data

Mar. 28, 2018   (WO) ................ PCT/CN2018/080889

(51) Int. Cl.
| | | |
|---|---|---|
| C07D 213/70 | (2006.01) | |
| A61K 31/426 | (2006.01) | |
| A61K 31/4418 | (2006.01) | |
| A61K 31/522 | (2006.01) | |

(52) U.S. Cl.
CPC .......... *C07D 213/70* (2013.01); *A61K 31/426* (2013.01); *A61K 31/4418* (2013.01); *A61K 31/522* (2013.01); *C07B 2200/13* (2013.01)

(58) Field of Classification Search
CPC .......................... C07D 213/70; C07B 2200/13; A61K 31/426; A61K 31/4418; A61K 31/522
See application file for complete search history.

(56) References Cited

U.S. PATENT DOCUMENTS 9,809,580 B2 * 11/2017 Jiang .................. A61P 5/18
9,856,239 B1   1/2018 Jiang

FOREIGN PATENT DOCUMENTS

| JP | 2017-524704 | 8/2017 |
|---|---|---|
| WO | 2011159839 A2 | 12/2011 |
| WO | 2011159840 A2 | 12/2011 |
| WO | 2016023460 A1 | 2/2016 |

OTHER PUBLICATIONS

Bhattacharya et al., Polymorphism in Pharmaceutical Solids: Thermoanalytical and Crystallographic Methods 334 (Brittain H. ed., 2d ed. Informa Healthcare USA, Inc. 2009) (1999) (Year: 1999).*
Ivanisevic, I., Pharm. Form. Qual. 30-33, 32 (2011) (Year: 2011).*
Rolf Hilfiker et al., "Relevance of Solid-state properties for Pharmaceutical Products", Polymorphism: in the Pharmaceutical Industry, 2006, WILEY-VCH Verlang GmbH & Co. KGaA, 19 pages.
Mino R. Caira, "Crystalline Polymorphism of Organic Compounds", Department of Chemistry, University of Cape Town, Rondebosch 7700, South Africa, Topics in Current Chemistry, vol. 198 (1998), 46 pages.
International Search Report for PCT/CN2019/079619 dated Jun. 25, 2019, 5 pages.
Written Opinion of the ISA for PCT/CN2019/079619 dated Jun. 25, 2019, 5 pages.
Notice of Reasons for Rejection dated Mar. 13, 2023 in Japanese Application No. 2020-551976, 6 pages (with English Translation).
Berge et al., "Pharmaceutical Salts", Journal of Pharmaceutical Sciences, vol. 66, No. 1, Jan. 1977, pp. 1-19.
Yakuzaigaku, Japanese Journal of Pharmaceutical Science and Technology, vol. 66, No. 6. 2006, pp. 435-439 (with partial English Translation).

* cited by examiner

*Primary Examiner* — Timothy R Rozof
(74) *Attorney, Agent, or Firm* — Nixon & Vanderhye, P.C.

(57) ABSTRACT

Provided herein are compounds, salts, crystalline forms, and pharmaceutical compositions that are related to thiobutyrate compounds, such as Compound (1) and its salts (such as sodium, potassium, and calcium salt), as well as methods of preparing the same. Also provided herein are methods of using the compounds, salts, crystalline forms, and pharmaceutical compositions for the treatment of diseases or disorders, such as gout and hyperuricemia.

19 Claims, 11 Drawing Sheets

SALT FORMS OF URAT-1 INHIBITORS

CROSS REFERENCE TO RELATED APPLICATIONS

Figure 1A:
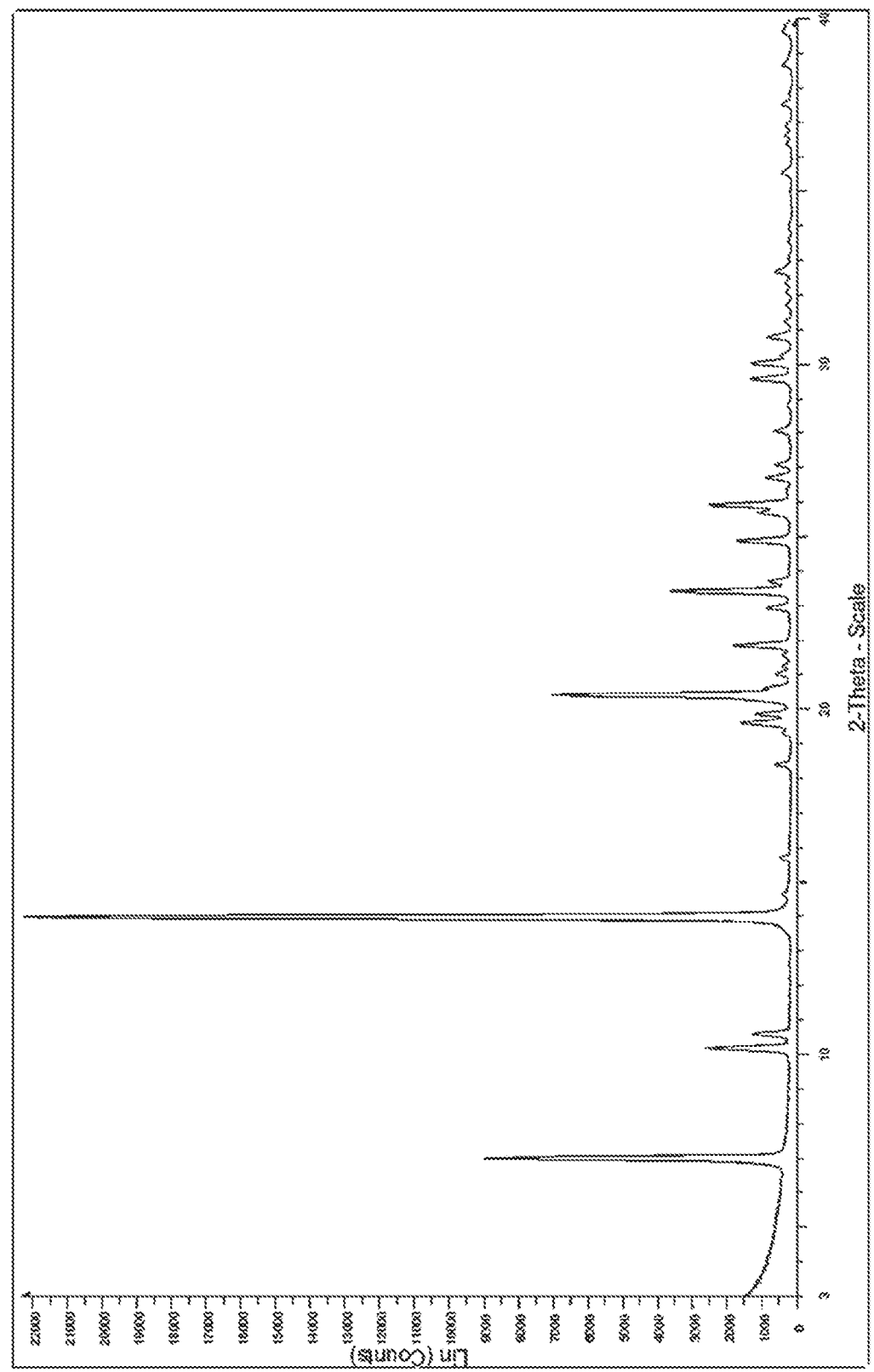

This application is a continuation of U.S. application Ser. No. 17/041,855, filed Sep. 25, 2020, which is a U.S. national phase of International Application No. PCT/CN2019/079619 filed Mar. 26, 2019 which designated the U.S. and claims priority to International Application No. PCT/CN2018/080889 filed Mar. 28, 2018, the entire contents of each of which are hereby incorporated by reference.

BACKGROUND OF THE INVENTION

Field of the Invention

In various embodiments, the present invention generally relates to novel salts of URAT-1 inhibitors, pharmaceutical compositions comprising the same, and methods of preparation and use thereof.

Background Art

Uric acid is the final metabolite of purine in human body. Uric acid is present in blood mainly in the form of its sodium salt. Serum uric acid level in human is generally lower than 6 mg/dL. When uric acid level in serum exceeds 7 mg/dL (Shi, et al., Nature 2003, 425:516-523), sodium salt of uric acid can crystallize out and precipitate on joints and other parts of the body, which can result in diseases or disorders such as gout, urinary stones, and kidney stones, etc. Patients with such diseases or disorders are often accompanied with other complications. For example, gout patients often also have complications such as hypertension, diabetes, hyperlipidemia, dyslipidemia, atherosclerosis, obesity, metabolic disease, nephropathy, cardiovascular disease, and respiratory disease, etc. (Rock, Et al., Nature Reviews Rheumatology 2013, 9:13-23).

In 2002, Japanese scientists (Endou group) reported that anion transport channel protein URAT1 is a major protein responsible for reabsorption of uric acid in kidney. The same group also found that the blood uric acid level in people with certain URAT1 gene mutation that leads to lower protein concentration or nonfunctional proteins is only one-tenth of that observed in normal people (Enomoto et al., Nature 2002 417:447-452). These human genetics evidence further demonstrates that URAT1 anion transport protein in kidney plays very important role in regulating the concentration of uric acid in blood.

Human urate anion transporter 1, hURAT1, a member of anion transporter family, is located at luminal surface side of epithelial cells of renal proximal convoluted tubules, mainly participates in the reabsorption of uric acid in renal proximal convoluted tubules. URAT1 accomplishes reabsorption of uric acid and excretion of small amount of uric acid by exchanging univalent anions within cells with uric acid in lumens. Anion transport channel proteins located in renal proximal convoluted tubules also comprise anion transport channel protein OAT4, which has 42% of similarity with URAT1 (amino acids of protein). Generally, a URAT1 inhibitor also has inhibitory effect on OAT4 and some other anion transport channel proteins that also reabsorb uric acid back to the blood from renal tubules.

The above shows that inhibiting URAT1 is a very good and specific strategy for reducing blood uric acid level and treat related diseases or disorders such as gout. Certain drugs and candidates such as benzbromarone, probenecid, and lesinurad are inhibitors of kidney URAT1 anion transport channel protein, which can help achieve one objective in the treatment of gout and its accompanying complications, which is to reduce blood uric acid levels to not greater than 6 mg/dL. This represents an addition to the method of inhibiting Xanthine oxidase by compounds such as allopurinol and febuxostat, which reduce blood uric acid levels by reducing the production of uric acid.

BRIEF SUMMARY OF THE INVENTION

U.S. Pat. No. 9,809,580 describes various thio-substituted carboxylic acids such as thiobutyric acid compounds that are effective in inhibiting URAT1 and are useful in treating diseases or disorders such as gout and hyperuricemia. In various embodiments, the present invention is directed to thio-substituted carboxylic acids and pharmaceutically acceptable salts thereof, for example, in a crystalline form and/or as a substantially pure isolated salt, pharmaceutical compositions comprising the same, methods of preparing the same, and methods of using the same.

Certain specific embodiments of the present invention are directed to Compound 1 (2-(1-(((3-(4-cyanophenyl)pyridin-4-yl)thio)methyl)cyclopropyl)acetic acid), or its pharmaceutically acceptable salt, such as sodium salt, potassium salt, or calcium salt.

Compound 1 and its pharmaceutically acceptable salts herein can be substantially pure. For example, in some embodiments, the present invention provides a substantially pure Compound 1. In some embodiments, the present invention provides a substantially pure salt of Compound 1, for example, a substantially pure sodium salt of Compound 1 (Compound 1-Na), a substantially pure potassium salt of Compound 1 (Compound 1-K), or a substantially pure calcium salt of Compound 1 (e.g., Compound 1-Ca).

In any of the embodiments described herein, Compound 1 or its pharmaceutically acceptable salts can be in a crystalline form. For example, in some embodiments, a substantially pure Compound 1 can comprise, consist essentially of, or consist of Form I of Compound 1. In some embodiments, a substantially pure Compound 1-Na can comprise, consist essentially of, or consist of Form II of Compound 1-Na. In some embodiments, a substantially pure Compound 1-K can comprise, consist essentially of, or consist of Form III of Compound 1-K. In some embodiments, a substantially pure Compound 1-Ca can comprise, consist essentially of, or consist of Form IV of Compound 1-Ca. The crystalline forms Form I, II, III, and IV are defined herein.

In some embodiments, the present invention provides a pharmaceutical composition comprising Compound 1 or a pharmaceutically acceptable salt thereof. For example, in some embodiments, the pharmaceutical composition can comprise, consist essentially of, or consist of one or more of the substantially pure compounds herein (e.g., Compound 1, 1-Na, 1-K, or 1-Ca) and optionally a pharmaceutically acceptable excipient or carrier. In some embodiments, the pharmaceutical composition can comprise, consist essentially of, or consist of one or more of the crystalline forms selected from Form I of Compound 1, Form II of Compound 1-Na, Form III of Compound 1-K, and Form IV of Compound 1-Ca and optionally a pharmaceutically acceptable excipient or carrier.

Certain specific embodiments are directed to pharmaceutical compositions comprising a therapeutically effective amount of Compound 1-Na, e.g., in crystalline Form II. In some embodiments, the active ingredient of the pharmaceutical composition can comprise, consist essentially of, or consist of Compound 1-Na. In some embodiments, Compound 1-Na in the pharmaceutical composition exists in Form II. In some embodiments, the pharmaceutical composition is substantially free of solid forms of Compound 1-Na other than Form II. In some embodiments, the pharmaceutical composition is substantially free of Compound 1. In some embodiments, the pharmaceutical composition is substantially free of a non-sodium salt of Compound 1.

The pharmaceutical compositions described herein can be formulated for any suitable routes of administration. In some embodiments, the pharmaceutical composition can be formulated for oral administration. For example, in any of the embodiments described herein, the pharmaceutical composition can be formulated in the form of a tablet or a capsule. In some embodiments, the pharmaceutical composition can be enteric coated. However, in some embodiments, the pharmaceutical composition can be non-enteric coated.

The compounds, salts, and crystalline forms described herein can be used alone, in combination with each other, or with a second agent. For example, in some embodiments, the pharmaceutical composition described herein can include a second agent selected from a xanthine oxidase inhibitor, a xanthine dehydrogenase inhibitor, a xanthine oxidoreductase inhibitor, and combinations thereof. In any of the embodiments described herein, the second agent can be allopurinol, febuxostat or a combination thereof.

Certain embodiments of the present invention are directed to methods of using the compounds, salts, crystalline forms, and/or pharmaceutical compositions herein for treating diseases or disorders associated with abnormal uric acid levels. In some embodiments, the method comprises administering to a subject in need thereof a therapeutically effective amount of one or more of the compounds described herein (e.g., Compound 1, 1-Na, 1-K, or 1-Ca), for example, the substantially pure compounds herein, the crystalline forms herein; or a therapeutically effective amount of any of the pharmaceutical compositions described herein. In some embodiments, the method is for treating one or more diseases or disorders chosen from gout, gouty arthritis, recurrent gout attack, hyperuricemia, joint inflammation, arthritis, urolithiasis, kidney disease, kidney stone, kidney failure, hypertension, cardiovascular disease, coronary heart disease, Lesch-Nyhan syndrome, Kelley-Seegmiller syndrome, plumbism, hyperparathyroidism, psoriasis and sarcoidosis. In some embodiments, the method is for lowering blood levels of uric acid or promoting excretion of uric acid. In some specific embodiments, the method is for treating gout. In some specific embodiments, the method is for treating hyperuricemia. The methods described herein are not limited to any specific routes of administration. For example, in any of the embodiments described herein, the administration can be oral administration.

In some embodiments, the methods herein can further include administering a second agent (e.g., described herein) to the subject in need thereof. In some embodiments, the second agent can be administered concurrently or sequentially.

BRIEF DESCRIPTION OF THE DRAWINGS/FIGURES

Figure 1B:
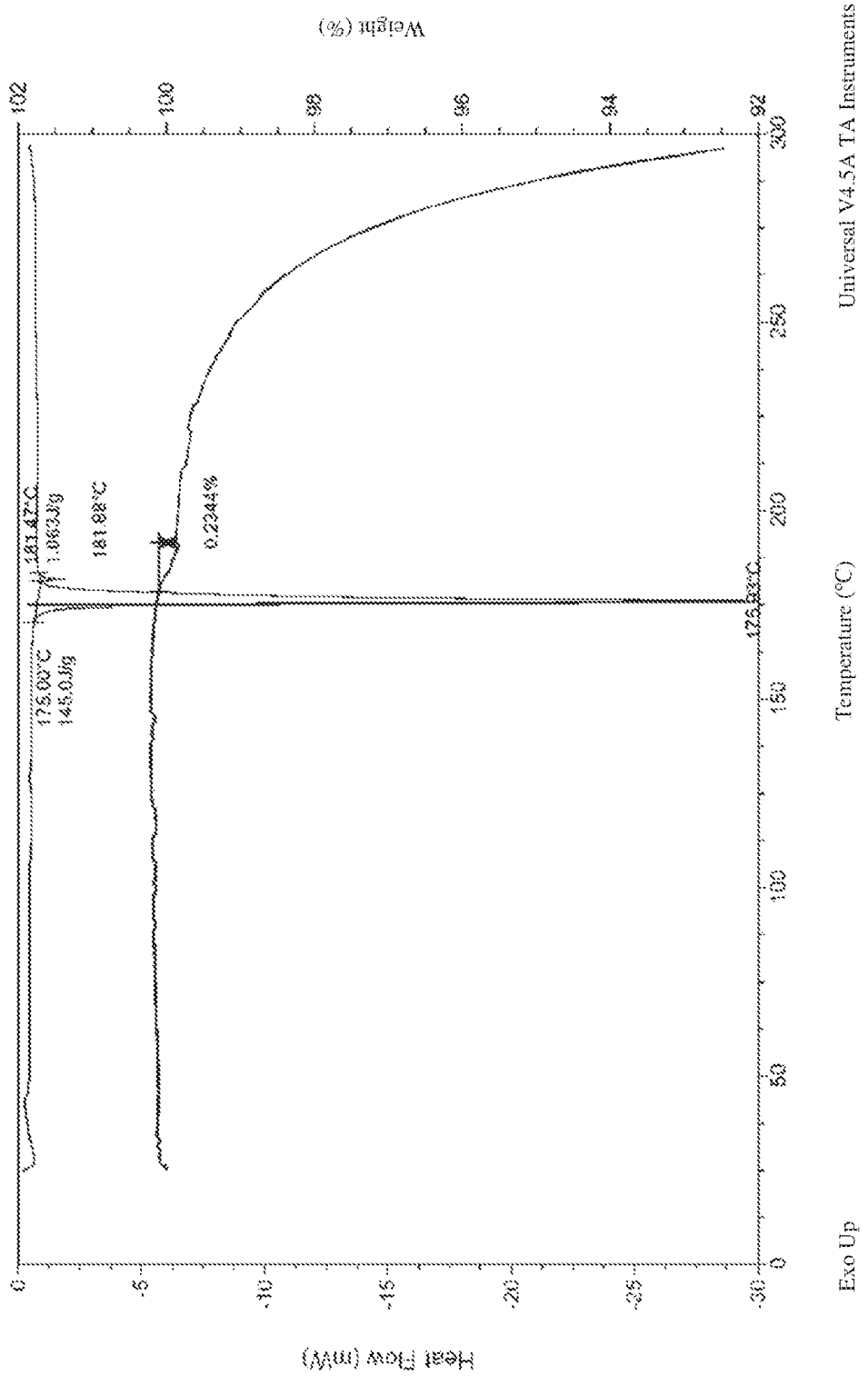

FIG. 1A shows a representative X-ray powder diffraction (XRPD) spectrum of crystalline form I of Compound 1 (2-(1-(((3-(4-cyanophenyl)pyridin-4-yl)thio)methyl)cyclopropyl)acetic acid). FIG. 1B shows a representative thermogravimetric analysis (TGA) and differential scanning calorimetry (DSC) analysis of crystalline form I of Compound 1.

Figure 2A:
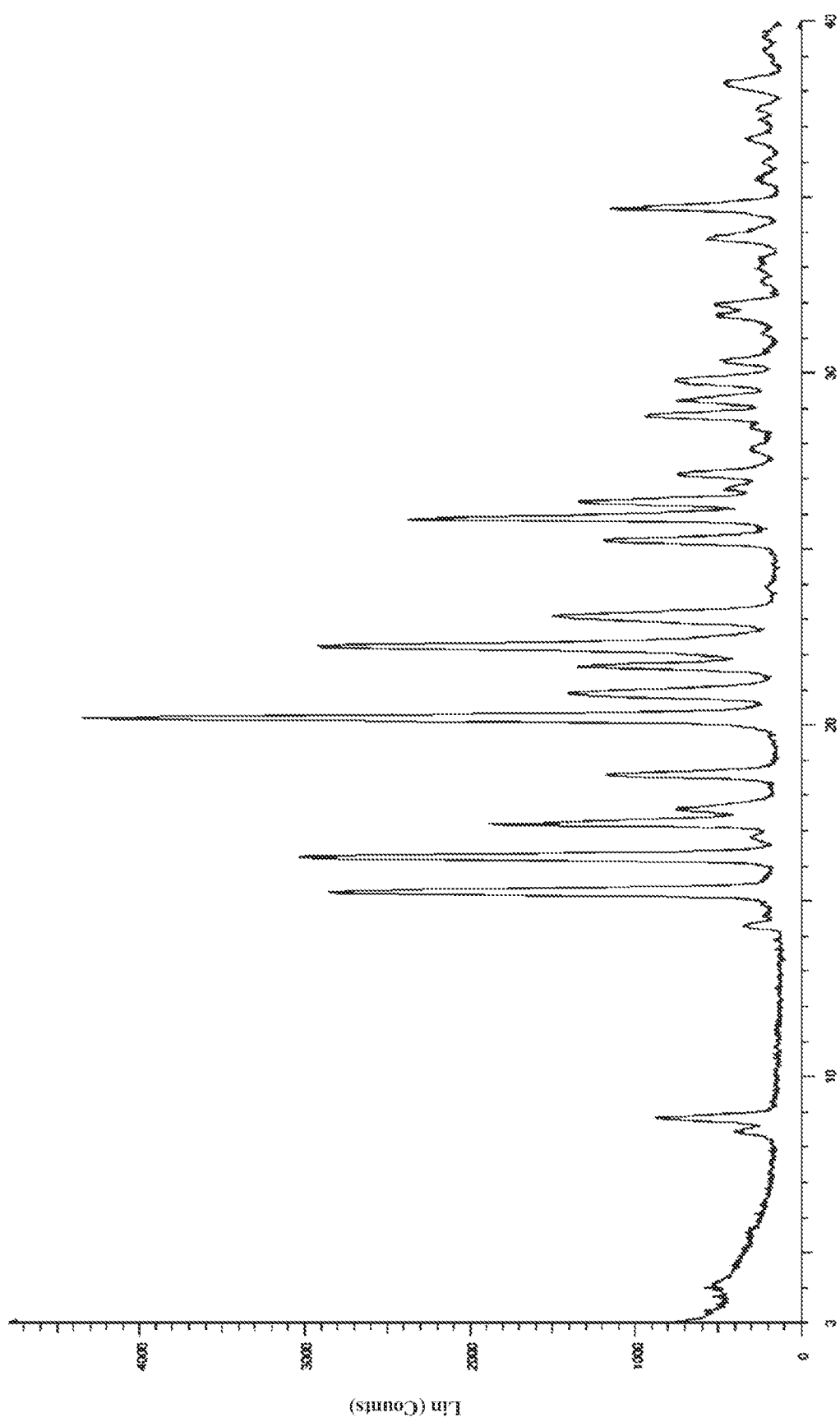
Figure 2B:
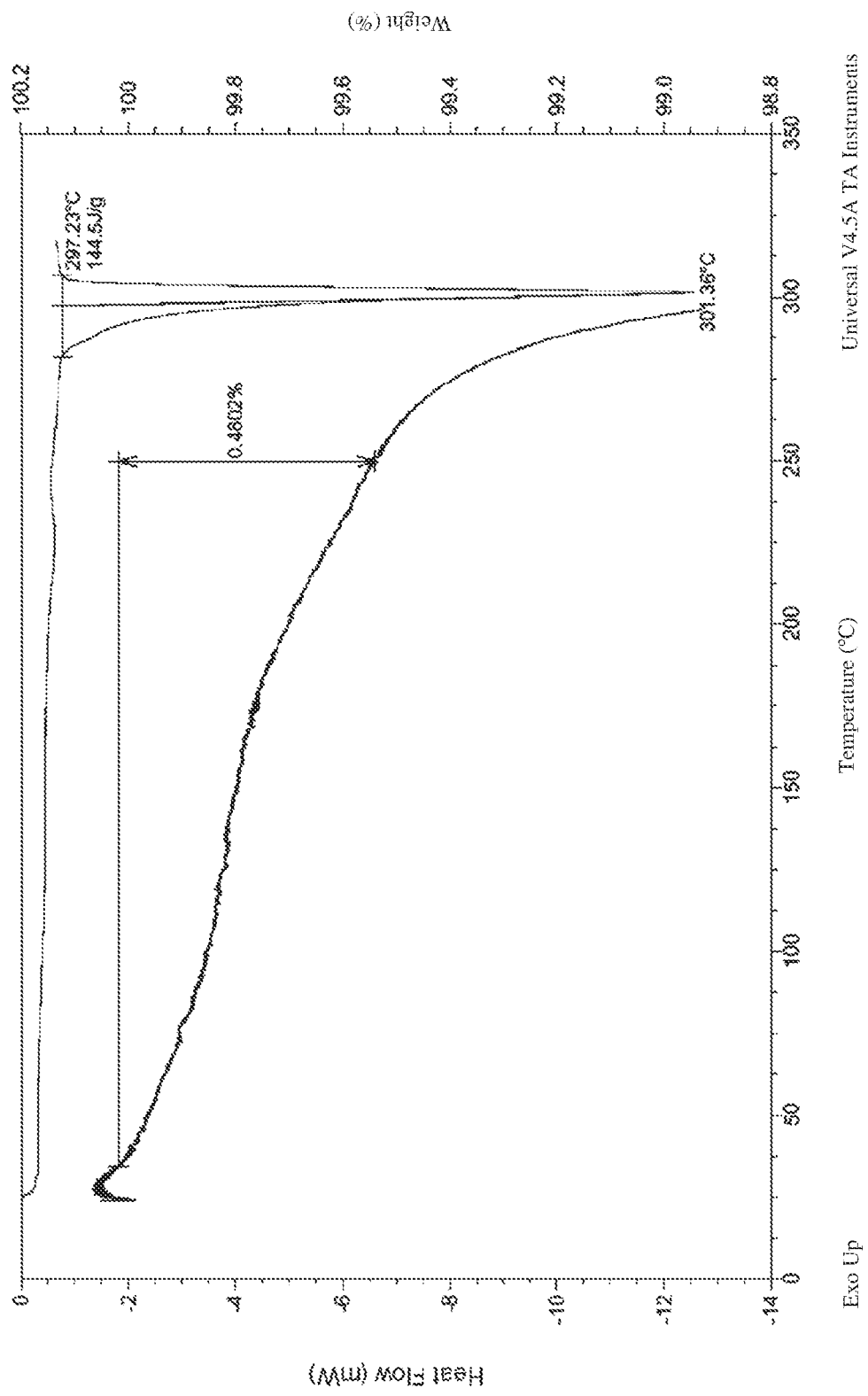
Figure 2C:
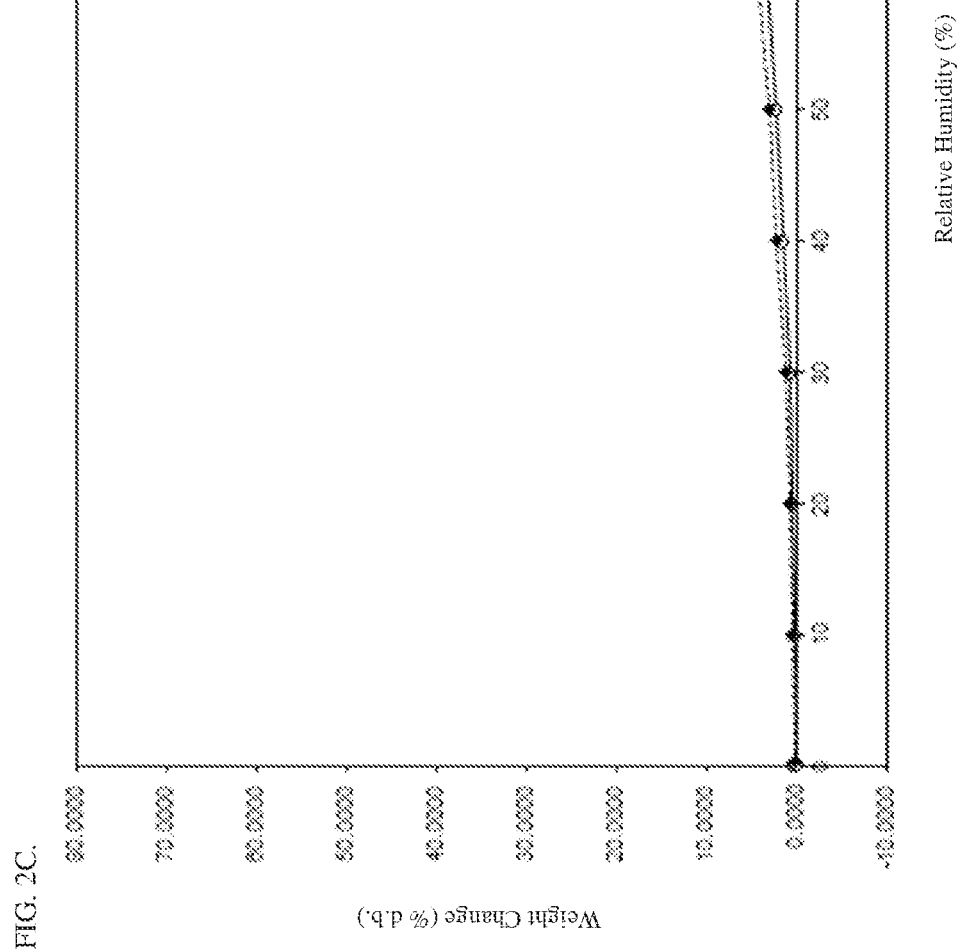

FIG. 2A shows a representative XRPD spectrum of crystalline form II of Compound 1-Na (sodium 2-(1-(((3-(4-cyanophenyl)pyridin-4-yl)thio)methyl)cyclopropyl)acetate). FIG. 2B shows a representative TGA and DSC analysis of crystalline form II of Compound 1-Na. FIG. 2C shows a representative dynamic moisture sorption (DVS) spectrum of Compound 1-Na.

Figure 3A:
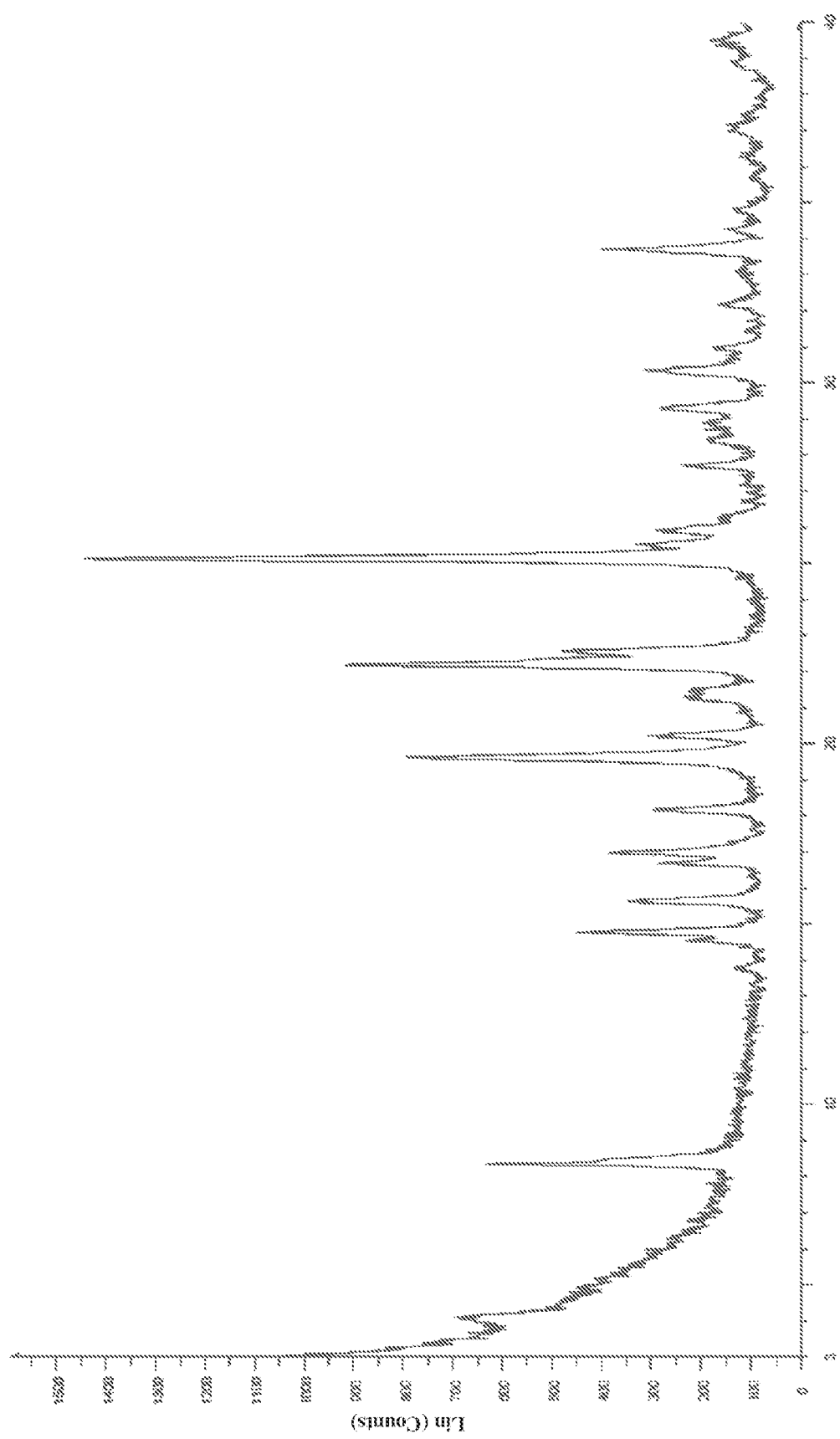
Figure 3B:
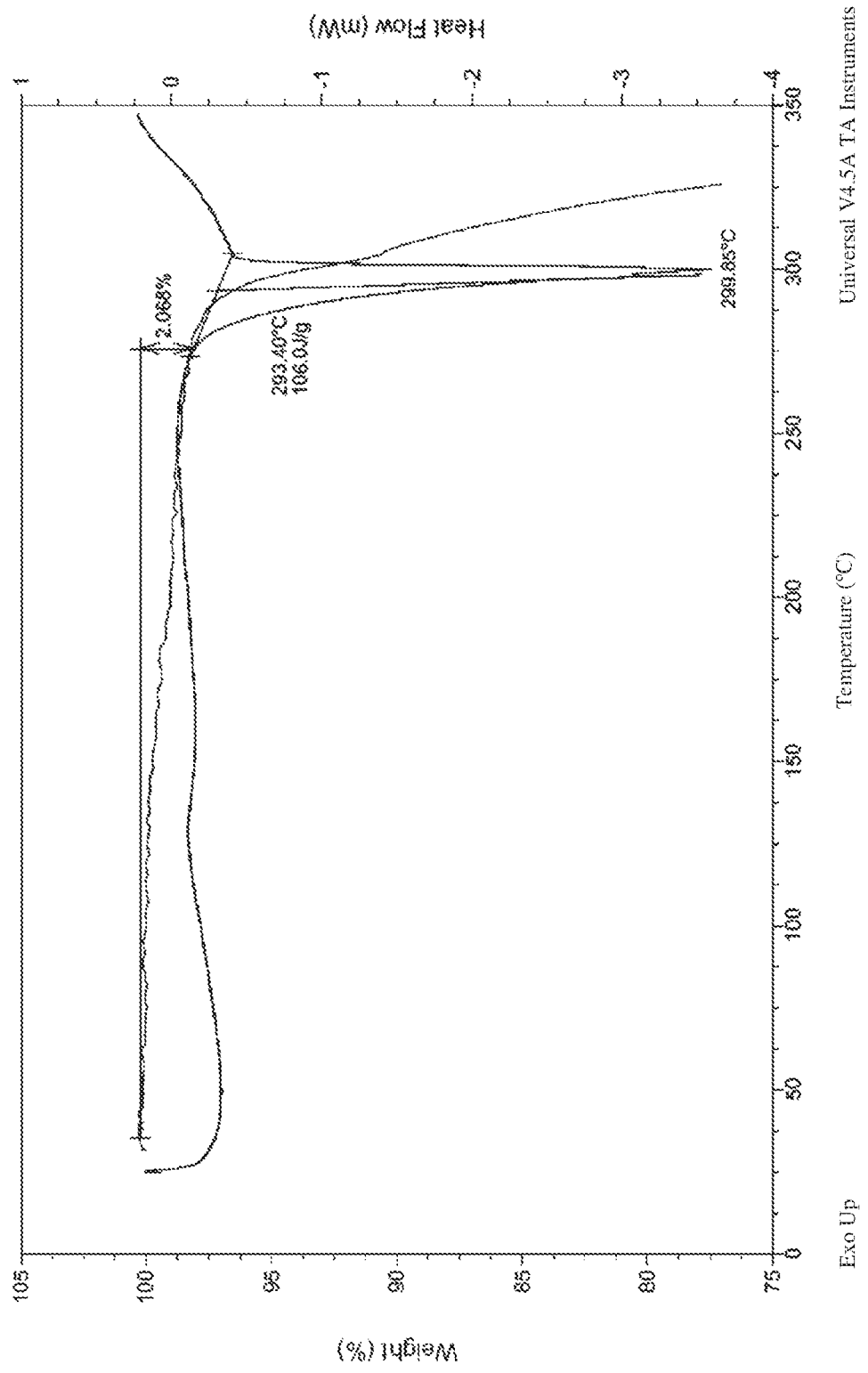
Figure 3C:
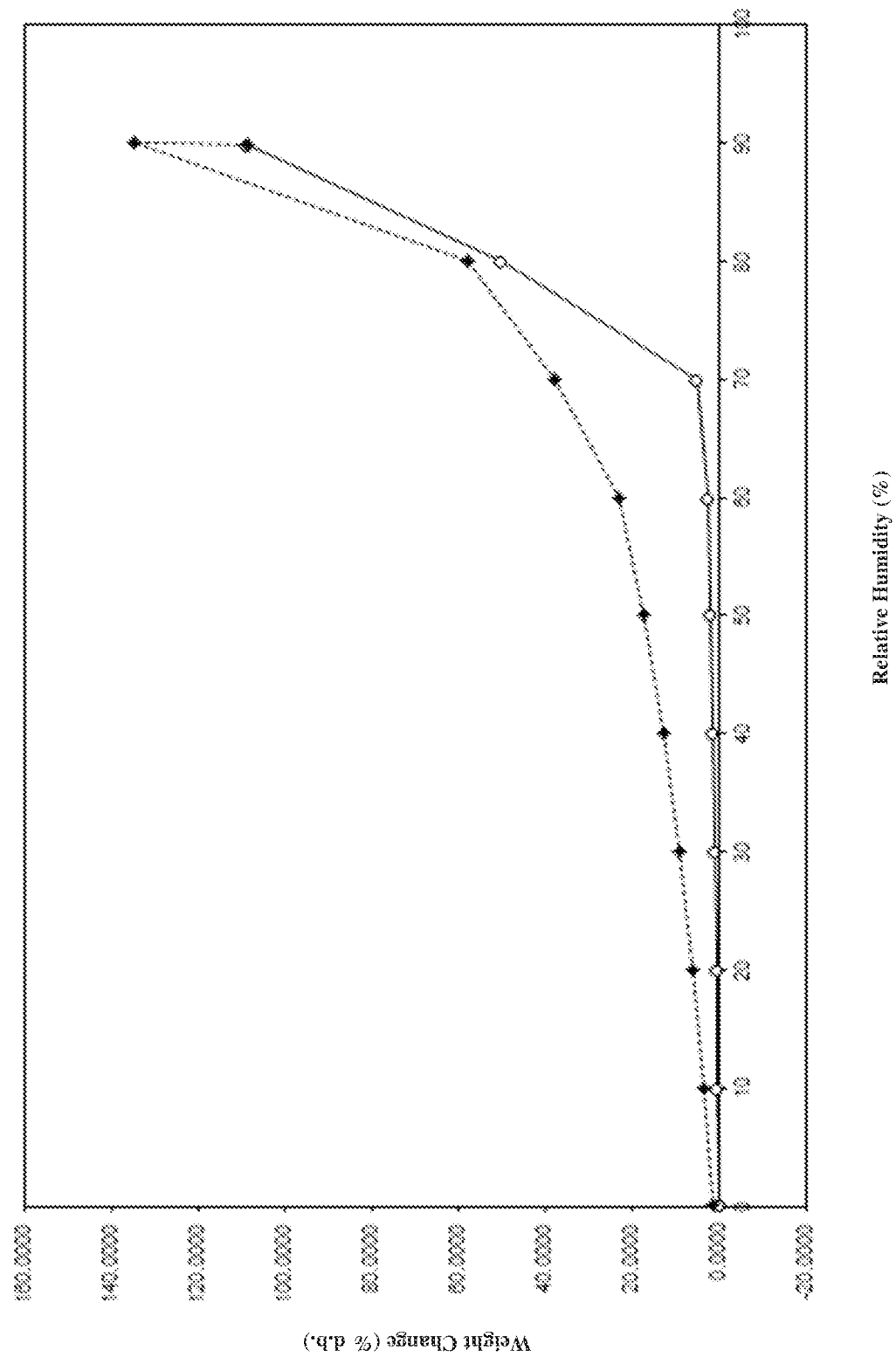

FIG. 3A shows a representative XRPD spectrum of crystalline form III of Compound 1-K (potassium 2-(1-(((3-(4-cyanophenyl)pyridin-4-yl)thio)methyl)cyclopropyl)acetate). FIG. 3B shows a representative TGA and DSC analysis of crystalline form III of Compound 1-K. FIG. 3C shows a representative DVS spectrum of Compound 1-K.

Figure 4A:
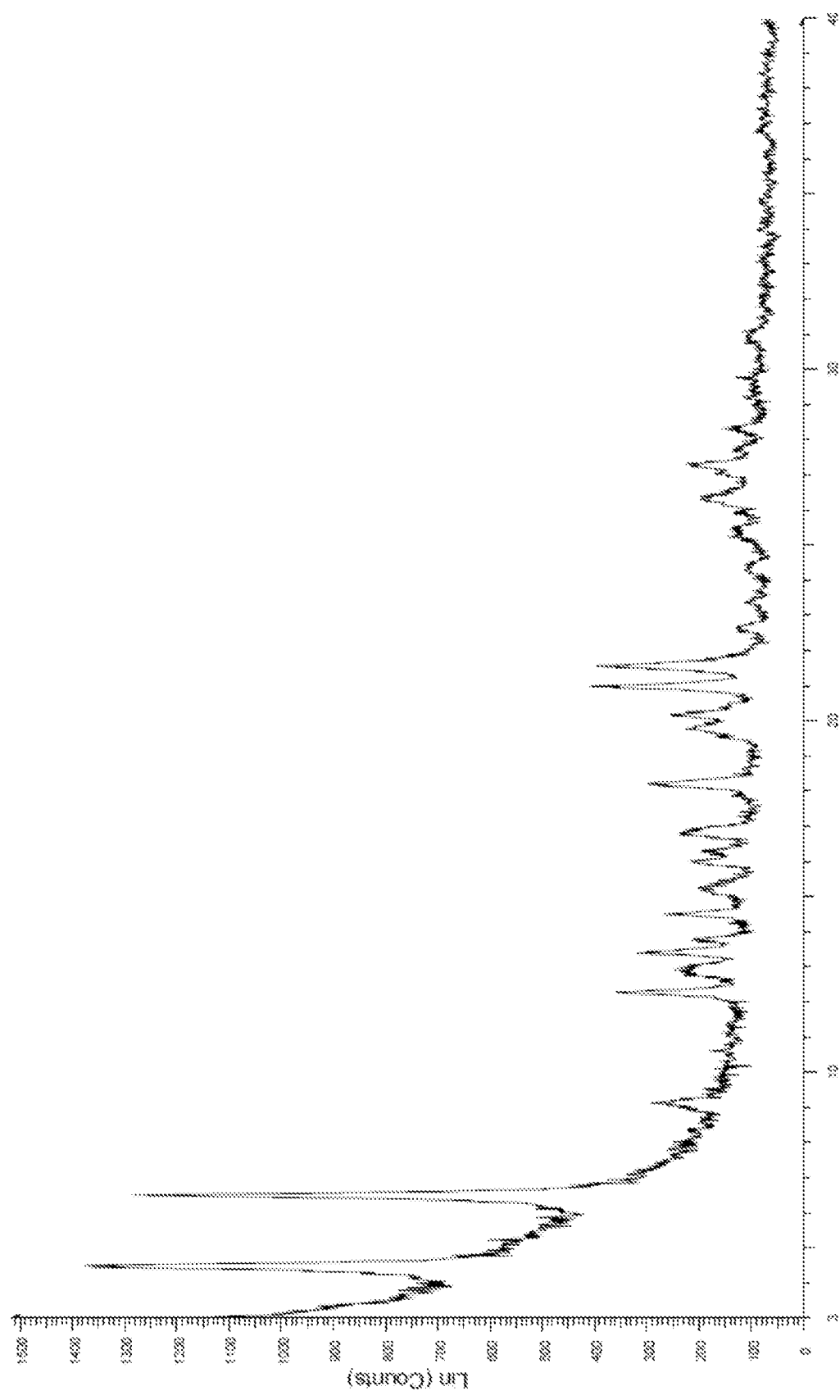
Figure 4B:
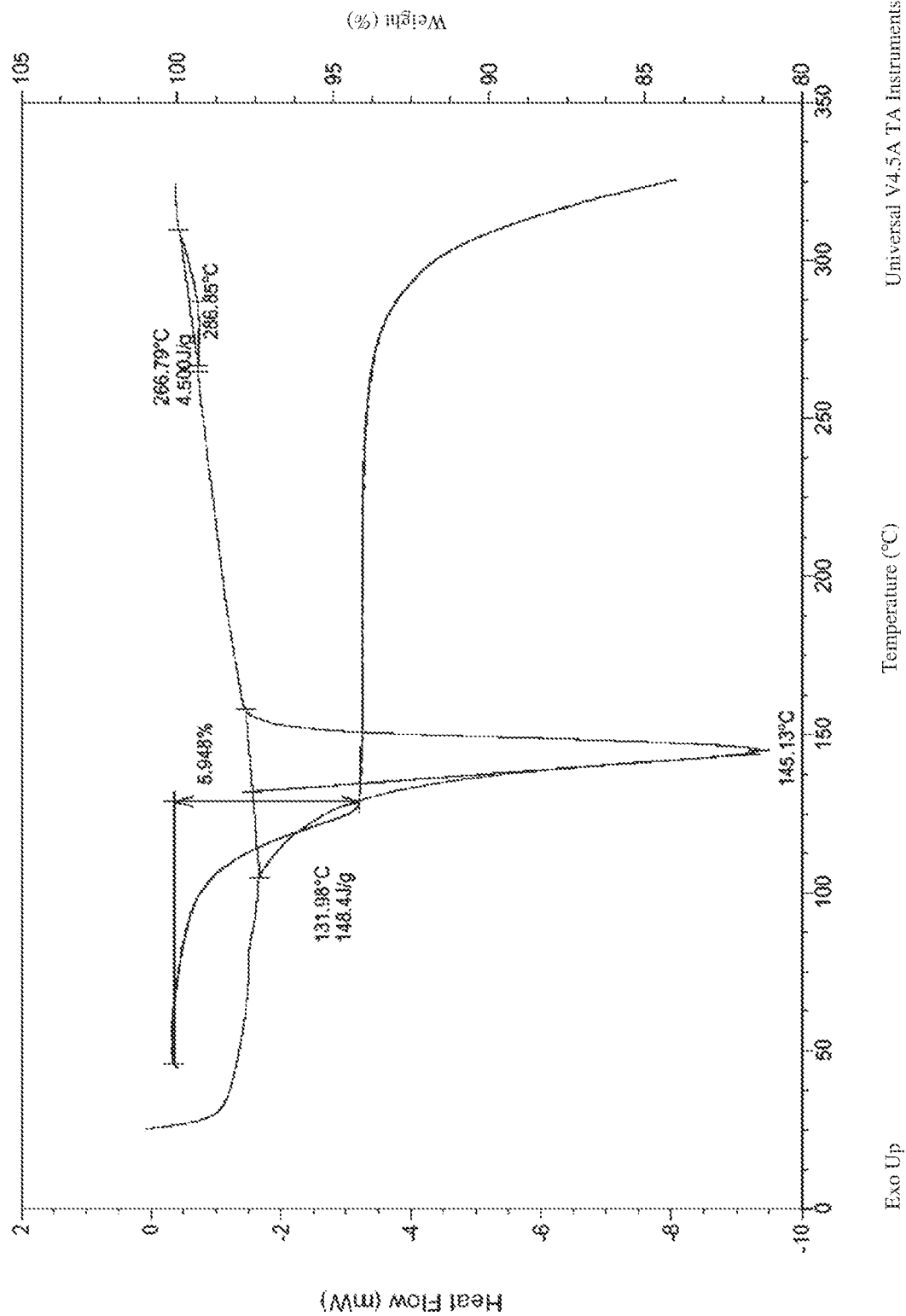
Figure 4C:
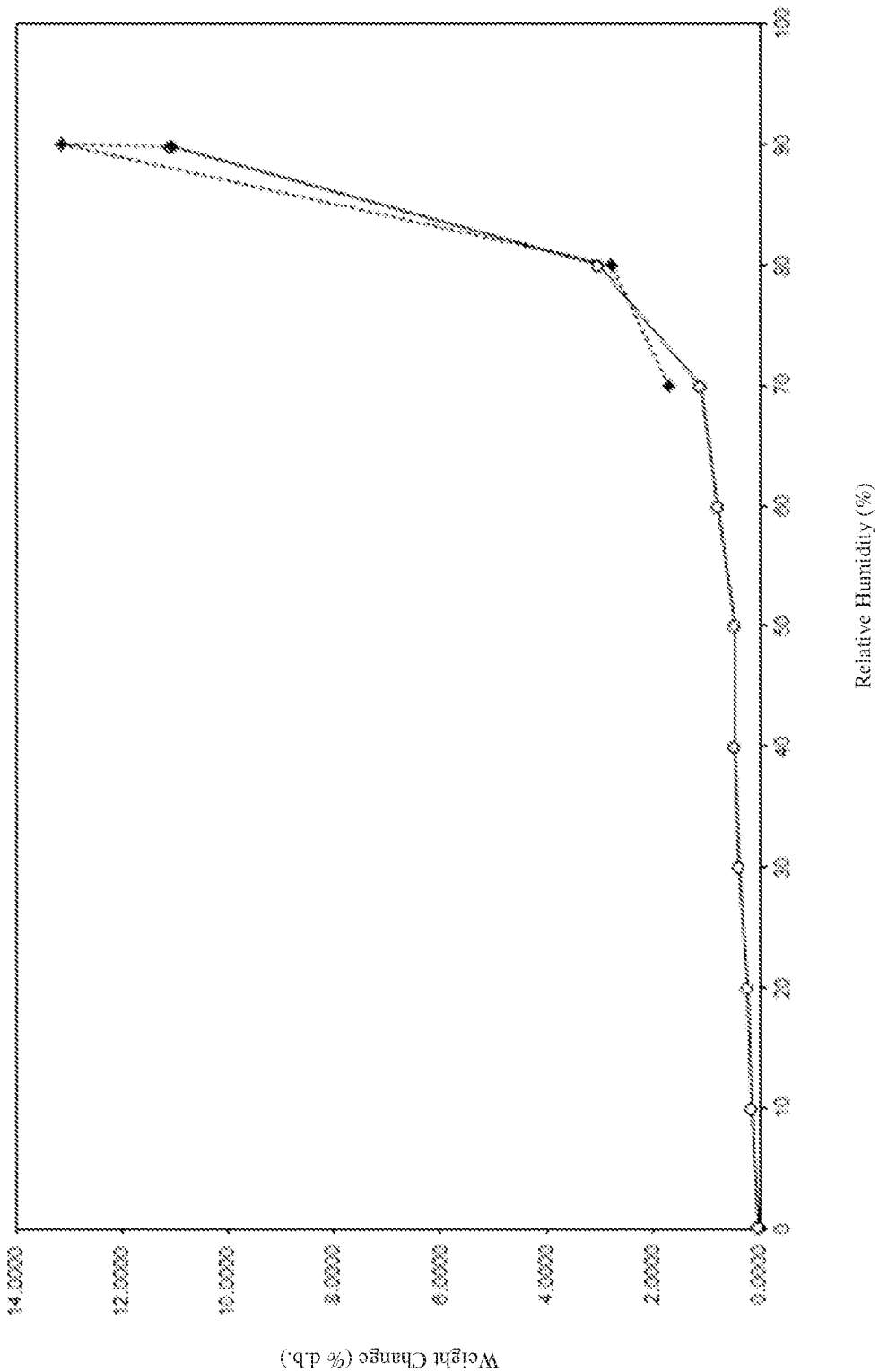

FIG. 4A shows a representative XRPD spectrum of crystalline form IV of Compound 1-Ca (calcium 2-(1-(((3-(4-cyanophenyl)pyridin-4-yl)thio)methyl)cyclopropyl)acetate). FIG. 4B shows a representative TGA and DSC analysis of crystalline form IV of Compound 1-Ca. FIG. 4C shows a representative DVS spectrum of Compound 1-Ca.

DETAILED DESCRIPTION OF THE INVENTION

In various embodiments, thio-substituted carboxylic acid compounds and pharmaceutically acceptable salts, for example, in a crystalline form or as a substantially pure compound, are provided. Also provided are pharmaceutical compositions, methods of preparation, and methods of using the same. More specific embodiments are directed to 2-(1-(((3-(4-cyanophenyl)pyridin-4-yl)thio)methyl)cyclopropyl) acetic acid and its pharmaceutically acceptable salt, such as sodium salt, potassium salt, or calcium salt.

Compounds/Salts

In various embodiments, the present invention is directed to salts (e.g., sodium, potassium, or calcium salt) of thio-substituted carboxylic acid compounds that are effective inhibitors of URAT-1 and are useful in treating various diseases and disorders, such as gout or hyperuricemia. Examples of such carboxylic acid compounds were previously described in U.S. Pat. No. 9,809,580, the content of which is hereby incorporated by reference in its entirety.

In some specific embodiments, the present invention provides salts (e.g., sodium, potassium, or calcium salt) of Compound 1. Compound 1, with a chemical name 2-(1-(((3-(4-cyanophenyl)pyridin-4-yl)thio)methyl)cyclopropyl)acetic acid, and a structure shown below, is a potent inhibitor of URAT-1 and is useful in treating various diseases and disorders, such as gout or hyperuricemia.

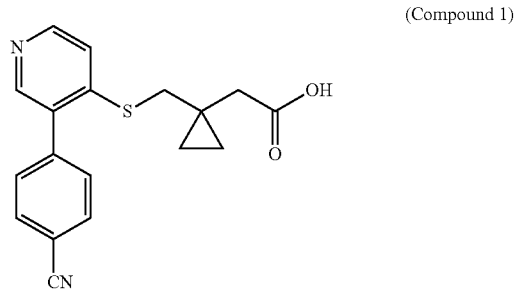 [SMILES: N#Cc1ccc(-c2cnccc2SCC2(CC(=O)O)CC2)cc1]

(Compound 1)

In some embodiments, an isolated salt (e.g., sodium, potassium, or calcium salt) of Compound 1 is provided. In some embodiments, the isolated salt is a sodium salt. In some embodiments, the isolated salt is a potassium salt. In some embodiments, the isolated salt is a calcium salt.

The isolated salt herein can be substantially pure. For example, in some embodiments, the isolated salt of Compound 1 (e.g., sodium salt or potassium salt) is characterized by a purity by weight and/or by HPLC area of at least 70% (e.g., at least 75%, at least 80%, at least 85%, at least 90%, at least 95%, at least 97%, or at least 99%). In some embodiments, the isolated salt of compound 1 (e.g., sodium salt or potassium salt) is characterized by a purity by weight and/or by HPLC area of about 70%, about 75%, about 80%, about 85%, about 90%, about 95%, about 97%, about 99%, or any ranges between the specified values. Unless otherwise obvious from context, for the purpose of calculating the weight percentage of the compound/salt in the substantially pure compound or salt, anything other than the compound or salt, or a solvate or hydrate form thereof, is regarded as an impurity, which includes for example residual solvents, moisture contents, etc. For avoidance of doubt, a composition comprising the substantially pure compound or salt herein and one or more other ingredients should be understood as a composition obtained directly or indirectly from mixing the substantially pure compound or salt herein with the one or more other ingredients, such as water, pharmaceutically acceptable excipients, etc.

In some specific embodiments, the present invention is directed to the sodium salt of Compound 1, designated herein as Compound 1-Na, which has a chemical name of sodium 2-(1-(((3-(4-cyanophenyl)pyridin-4-yl)thio)methyl) cyclopropyl)acetate and a structure represented below:

(Compound 1-Na)

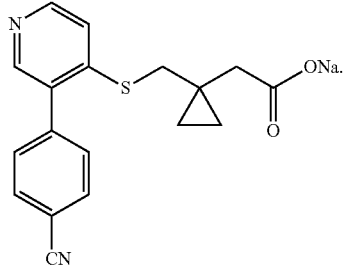

In some embodiments, the present invention provides a substantially pure Compound 1-Na. In some embodiments, the substantially pure Compound 1-Na has a purity by weight and/or by HPLC area of at least 70% (e.g., at least 75%, at least 80%, at least 85%, at least 90%, at least 95%, at least 97%, or at least 99%). In some embodiments, the substantially pure Compound 1-Na has a purity by weight and/or by HPLC area of about 70%, about 75%, about 80%, about 85%, about 90%, about 95%, about 97%, about 99%, or any ranges between the specified values.

The substantially pure Compound 1-Na can be prepared from a substantially pure Compound 1. Compound 1 can be prepared in high purity according to the process disclosed herein. Typically, Compound 1 prepared according to the processes herein has a total impurity of less than 1% (e.g., less than 0.8%, less than 0.5%, less than 0.2%) as measured by HPLC. In some embodiments, Compound 1 does not contain a single impurity in an amount greater than 1% (e.g., not greater than 0.8%, not greater than 0.5%, not greater than 0.2%) as measured by HPLC. As shown in the Examples section, Compound 1 can be prepared in a crystalline form, e.g., Form I. In some embodiments, the substantially pure Compound 1-Na can be prepared from Form I of Compound 1. As used herein, Form I refers to a crystalline form of Compound 1 which can be characterized by an XRPD pattern substantially the same as FIG. 1A; an XRPD spectrum having the major peaks (e.g., peaks with relative intensity of 20% or above, 30% or above, 40% or above, 50% or above, 60% or above, 70% or above, 80% or above, or 90% or above) of FIG. 1A; an XRPD pattern having one or more (e.g., 1, 2, 3, 4, 5, 6, 7, 8, or all) of the following peaks: 7.0, 10.2, 10.6, 14.0, 20.4, 21.9, 23.4, 24.9, and 25.9 degrees 2 theta, ±0.2°; a DSC pattern having an endotherm peak with peak temperature at about 175.9° C.; a DSC profile substantially the same as shown in FIG. 1B; a TGA profile substantially the same as shown in FIG. 1B; or a combination thereof. Major peaks of an XRPD spectrum as used herein refer to peaks having diffraction angles between 4-30 degrees (2 theta) and a relative intensity of 10% or above. In some embodiments, major peaks of an XRPD spectrum can refer to peaks with a relative intensity of 20% or above, 30% or above, 40% or above, 50% or above, 60% or above, 70% or above, 80% or above, or 90% or above.

The substantially pure Compound 1-Na herein typically has a sodium content close to the theoretical sodium content calculated based on the formula of Compound 1-Na. In some embodiments, the substantially pure Compound 1-Na is characterized by a molar ratio of sodium to the carboxylate portion of Compound 1-Na of about 1:1. In some embodiments, the substantially pure Compound 1-Na has a sodium content of about 80% to about 125% of the theoretical sodium content. In some embodiments, the substantially pure Compound 1-Na has a sodium content by weight of about 6.0% to about 7.3%.

The substantially pure Compound 1-Na herein can be free or substantially free of Compound 1, and/or can be free or substantially free of other salts of Compound 1. In some embodiments, the substantially pure Compound 1-Na is substantially free of Compound 1, for example, with an amount of less than 5% by weight (e.g., less than 3%, less than 1%, less than 0.2%, less than 0.1% or less than 0.05%). In some embodiments, the substantially pure Compound 1-Na is free of Compound 1, other than an amount that may exist through equilibrium. In some embodiments, the substantially pure Compound 1-Na has no detectable amount of Compound 1. In some embodiments, the substantially pure Compound 1-Na is substantially free of other salts of Compound 1, for example, with an amount less than 5% by weight (e.g., less than 3%, less than 1%, less than 0.2%, less than 0.1% or less than 0.05%). In some embodiments, the substantially pure Compound 1-Na includes no detectable amount of other salts of Compound 1.

In some embodiments, the present invention provides a crystalline form II of Compound 1-Na. Form II of Compound 1-Na exhibited desirable stability, solubility, and other physicochemical profile, some of which are exemplified in the Examples section. As used herein, Form II refers to a crystalline form of Compound 1-Na which can be characterized by an XRPD pattern substantially the same as FIG. 2A; an XRPD spectrum having the major peaks (e.g., peaks with relative intensity of 20% or above, 30% or above, 40% or above, 50% or above, 60% or above, 70% or above, 80% or above, or 90% or above) of FIG. 2A; an XRPD spectrum having one or more (e.g., 1, 2, 3, 4, 5, 6, 7, 8, 9, 10, 11, 12, 13, 14) of the following peaks: 8.8, 15.2, 16.2, 17.2, 17.6, 18.6, 20.2, 20.9, 21.7, 22.2, 23.1, 25.2, 25.9, and 26.4 degrees 2 theta, ±0.2°; a DSC pattern having an endotherm peak with peak temperature at about 301.3° C.; a DSC profile substantially the same as shown in FIG. 2B; a TGA profile substantially the same as shown in FIG. 2B; or a combination thereof. For example, in some embodiments, the crystalline form II of Compound 1-Na is characterized by an XRPD spectrum having four or more of the following peaks: 8.8, 15.2, 16.2, 17.2, 17.6, 18.6, 20.2, 20.9, 21.7, 22.2, 23.1, 25.2, 25.9, and 26.4 degrees 2 theta, ±0.2°. In some embodiments, the crystalline form II of Compound 1-Na is characterized by an XRPD spectrum having eight or more of the following peaks: 8.8, 15.2, 16.2, 17.2, 17.6, 18.6, 20.2, 20.9, 21.7, 22.2, 23.1, 25.2, 25.9, and 26.4 degrees 2 theta, ±0.2°. In some embodiments, the crystalline form II of Compound 1-Na is characterized by an XRPD spectrum having all of the following peaks: 8.8, 15.2, 16.2, 17.2, 17.6, 18.6, 20.2, 20.9, 21.7, 22.2, 23.1, 25.2, 25.9, and 26.4 degrees 2 theta, ±0.2°. In some embodiments, the crystalline form II of Compound 1-Na is characterized by an XRPD spectrum substantially the same as shown in FIG. 2A. In any of the embodiments described herein, the substantially pure Compound 1-Na can consist essentially of Form II of Compound 1-Na. In any of the embodiments described herein, Compound 1-Na can exist in Form II. In any of the embodiments described herein, the substantially pure Compound 1-Na or a pharmaceutical composition comprising Compound 1-Na can include Compound 1-Na solely in the form of Form II, i.e., with no other solid form of Compound 1-Na identifiable by XRPD.

Exemplary methods for preparing crystalline Compound 1-Na are described herein. Typically, a substantially pure Compound 1 (e.g., in Form I) is dissolved in a solvent (e.g., THF) to form a solution; about 1 equivalent of NaOH (or another sodium base) is added to the solution to form Compound 1-Na; Compound 1-Na can then be precipitated out, for example, through reducing the amount of the solvent by evaporation. The NaOH (or another sodium base) can be added as a solid or in an aqueous or alcoholic (e.g., methanol or ethanol) solution. An example of preparation of Form II of Compound 1-Na is provided in the Examples section.

In some embodiments, Compound 1-Na can be recrystallized under suitable conditions. Suitable solvents for recrystallization include, but are not limited to, THF, toluene, MeOH, ethanol, n-propanol, isopropanol, isobutanol, methyl tert-butyl ether, ether, isoamylol, butyl acetate, ethyl formate, 1,4-dioxane, n-butanol, tert-butanol, n-heptane, cyclohexane, methyl isobutyl ketone, dimethylbenzene, isobutyl acetate, 2-butanone, acetonitrile, acetone, ethyl acetate, isopropyl acetate, and water. The solvents can be used alone or in various combinations. Recrystallization technics are generally known in the art.

In some specific embodiments, the present invention also provides the potassium salt of Compound 1, designated herein as Compound 1-K, which has a chemical name of potassium 2-(1-(((3-(4-cyanophenyl)pyridin-4-yl)thio) methyl)cyclopropyl)acetate and a structure represented below:

(Compound 1-K)

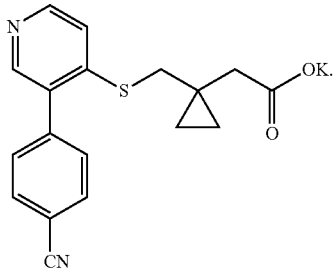

In some embodiments, the present invention provides a substantially pure Compound 1-K. In some embodiments, the substantially pure Compound 1-K has a purity by weight and/or by HPLC area of at least 70% (e.g., at least 75%, at least 80%, at least 85%, at least 90%, at least 95%, at least 97%, or at least 99%). In some embodiments, the substantially pure Compound 1-K has a purity by weight and/or by HPLC area of about 70%, about 75%, about 80%, about 85%, about 90%, about 95%, about 97%, about 99%, or any ranges between the specified values.

The substantially pure Compound 1-K can also be prepared from a substantially pure Compound 1. For example, in some embodiments, the substantially pure Compound 1-K can be prepared from Form I of Compound 1.

The substantially pure Compound 1-K herein typically has a potassium content close to the theoretical potassium content calculated based on the formula of Compound 1-K. In some embodiments, the substantially pure Compound 1-K is characterized by a molar ratio of potassium to the carboxylate portion of Compound 1-K of about 1:1. In some embodiments, the substantially pure Compound 1-K has a potassium content of about 80% to about 125% of the theoretical potassium content.

The substantially pure Compound 1-K herein can be free or substantially free of Compound 1, and/or can be free or substantially free of other salts of Compound 1. In some embodiments, the substantially pure Compound 1-K is substantially free of Compound 1, for example, with an amount of less than 5% by weight (e.g., less than 3%, less than 1%, less than 0.2%, less than 0.1% or less than 0.05%). In some embodiments, the substantially pure Compound 1-K is free of Compound 1, other than an amount that may exist through equilibrium. In some embodiments, the substantially pure Compound 1-K has no detectable amount of Compound 1. In some embodiments, the substantially pure Compound 1-K is substantially free of other salts of Compound 1, for example, with an amount less than 5% by weight (e.g., less than 3%, less than 1%, less than 0.2%, less than 0.1% or less than 0.05%). In some embodiments, the substantially pure Compound 1-K includes no detectable amount of other salts of Compound 1.

In some embodiments, the present invention provides a crystalline form III of Compound 1-K. Form III of Compound 1-K exhibited desirable stability, solubility, and other physicochemical profile, some of which are exemplified in the Examples section. As used herein, Form III refers to a crystalline form of Compound 1-K which can be characterized by an XRPD pattern substantially the same as FIG. 3A; an XRPD spectrum having the major peaks (e.g., peaks with relative intensity of 20% or above, 30% or above, 40% or above, 50% or above, 60% or above, 70% or above, 80% or above, or 90% or above) of FIG. 3A; an XRPD spectrum having one or more (e.g., 1, 2, 3, 4, 5, 6, 7, 8, 9, 10, or all) of the following peaks: 8.3, 14.5, 14.8, 15.6, 16.7, 17.0, 18.2, 19.6, 20.2, 22.2, 22.6, and 25.1 degrees 2 theta, ±0.2°; a DSC pattern having an endotherm peak with peak temperature at about 299.9° C.; a DSC profile substantially the same as shown in FIG. 3B; a TGA profile substantially the same as shown in FIG. 3B; or a combination thereof. For example, in some embodiments, the crystalline form III of Compound 1-K is characterized by an XRPD spectrum having four or more of the following peaks: 8.3, 14.5, 14.8, 15.6, 16.7, 17.0, 18.2, 19.6, 20.2, 22.2, 22.6, and 25.1 degrees 2 theta, ±0.2°. In some embodiments, the crystalline form III of Compound 1-K is characterized by an XRPD spectrum having eight or more of the following peaks: 8.3, 14.5, 14.8, 15.6, 16.7, 17.0, 18.2, 19.6, 20.2, 22.2, 22.6, and 25.1 degrees 2 theta, ±0.2°. In some embodiments, the crystalline form III of Compound 1-K is characterized by an XRPD spectrum having all of the following peaks: 8.3, 14.5, 14.8, 15.6, 16.7, 17.0, 18.2, 19.6, 20.2, 22.2, 22.6, and 25.1 degrees 2 theta, ±0.2°. In some embodiments, the crystalline form III of Compound 1-K is characterized by an XRPD spectrum substantially the same as shown in FIG. 3A. In any of the embodiments described herein, the substantially pure Compound 1-K can consist essentially of Form III of Compound 1-K. In any of the embodiments described herein, Compound 1-K can exist in Form III. In some embodiments, the substantially pure Compound 1-K or a pharmaceutical composition comprising Compound 1-K can include Compound 1-K solely in the form of Form III, i.e., with no other solid form of Compound 1-K identifiable by XRPD.

In some specific embodiments, the present invention also provides a calcium salt of Compound 1. In some embodiments, the calcium salt is Compound 1-Ca, which has a chemical name of calcium 2-(1-(((3-(4-cyanophenyl)pyridin-4-yl)thio)methyl)cyclopropyl)acetate and a structure represented below:

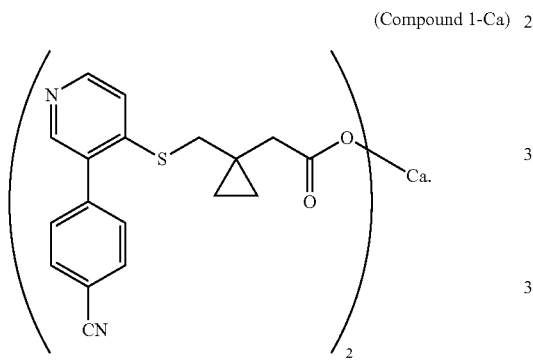

(Compound 1-Ca)

In some embodiments, the present invention provides a substantially pure Compound 1-Ca. In some embodiments, the substantially pure Compound 1-Ca has a purity by weight and/or by HPLC area of at least 70% (e.g., at least 75%, at least 80%, at least 85%, at least 90%, at least 95%, at least 97%, or at least 99%). In some embodiments, the substantially pure Compound 1-Ca has a purity by weight and/or by HPLC area of about 70%, about 75%, about 80%, about 85%, about 90%, about 95%, about 97%, about 99%, or any ranges between the specified values.

The substantially pure Compound 1-Ca can also be prepared from a substantially pure Compound 1. For example, in some embodiments, the substantially pure Compound 1-Ca can be prepared from Form I of Compound 1. Alternatively, the substantially pure Compound 1-Ca can also be prepared from a salt exchange reaction, for example, with Compound 1-K.

The substantially pure Compound 1-Ca herein typically has a calcium content close to the theoretical calcium content calculated based on the formula of Compound 1-Ca. In some embodiments, the substantially pure Compound 1-Ca is characterized by a molar ratio of calcium to the carboxylate portion of Compound 1-Ca of about 1:2. In some embodiments, the substantially pure Compound 1-Ca has a calcium content of about 80% to about 125% of the theoretical calcium content.

The substantially pure Compound 1-Ca herein can be free or substantially free of Compound 1, and/or can be free or substantially free of other salts of Compound 1. In some embodiments, the substantially pure Compound 1-Ca is substantially free of Compound 1, for example, with an amount of less than 5% by weight (e.g., less than 3%, less than 1%, less than 0.2%, less than 0.1% or less than 0.05%). In some embodiments, the substantially pure Compound 1-Ca is free of Compound 1, other than an amount that may exist through equilibrium. In some embodiments, the substantially pure Compound 1-Ca has no detectable amount of Compound 1. In some embodiments, the substantially pure Compound 1-Ca is substantially free of other salts of Compound 1, for example, with an amount less than 5% by weight (e.g., less than 3%, less than 1%, less than 0.2%, less than 0.1% or less than 0.05%). In some embodiments, the substantially pure Compound 1-Ca includes no detectable amount of other salts of Compound 1.

In some embodiments, the present invention provides a crystalline form IV of Compound 1-Ca. Form IV of Compound 1-Ca can also exist certain desirable stability, solubility, and other physicochemical profile, some of which are exemplified in the Examples section. As used herein, Form IV refers to a crystalline form of Compound 1-Ca which can be characterized by an XRPD pattern substantially the same as FIG. 4A; an XRPD spectrum having the major peaks (e.g., peaks with relative intensity of 20% or above, 30% or above, 40% or above, 50% or above, 60% or above, 70% or above, 80% or above, or 90% or above) of FIG. 4A; an XRPD spectrum having one or more (e.g., 1, 2, 3, 4, 5, 6, 7, 8, 9, 10, 11, 12, 13, or all) of the following peaks: 4.4, 6.5, 9.1, 12.3, 13.0, 13.4, 13.7, 14.5, 16.0, 16.8, 18.2, 19.8, 21.0, and 21.6 degrees 2 theta, ±0.2°; a DSC pattern having an endotherm peak with peak temperature at about 145.1° C.; a DSC profile substantially the same as shown in FIG. 4B; a TGA profile substantially the same as shown in FIG. 4B; or a combination thereof. For example, in some embodiments, the crystalline form IV of Compound 1-Ca is characterized by an XRPD spectrum having four or more of the following peaks: 4.4, 6.5, 9.1, 12.3, 13.0, 13.4, 13.7, 14.5, 16.0, 16.8, 18.2, 19.8, 21.0, and 21.6 degrees 2 theta, ±0.2°. In some embodiments, the crystalline form IV of Compound 1-Ca is characterized by an XRPD spectrum having eight or more of the following peaks: 4.4, 6.5, 9.1, 12.3, 13.0, 13.4, 13.7, 14.5, 16.0, 16.8, 18.2, 19.8, 21.0, and 21.6 degrees 2 theta, ±0.2°. In some embodiments, the crystalline form IV of Compound 1-Ca is characterized by an XRPD spectrum having all of the following peaks: 4.4, 6.5, 9.1, 12.3, 13.0, 13.4, 13.7, 14.5, 16.0, 16.8, 18.2, 19.8, 21.0, and 21.6 degrees 2 theta, +0.2°. In some embodiments, the crystalline form IV of Compound 1-Ca is characterized by an XRPD spectrum substantially the same as shown in FIG. 4A. In any of the embodiments described herein, the substantially pure Compound 1-Ca can consist essentially of Form IV of Compound 1-Ca. In any of the embodiments described herein, Compound 1-Ca can exist in Form IV. In some embodiments, the substantially pure Compound 1-Ca or a pharmaceutical composition comprising Compound 1-Ca can include Compound 1-Ca solely in the form of Form IV, i.e., with no other solid form of Compound 1-Ca identifiable by XRPD.

In some embodiments, the compounds described herein (e.g., Compound 1, 1-Na, 1-K, or 1-Ca) can exist in the form of a solvate or hydrate. For example, in some embodiments, the compounds described herein (e.g., Compound 1, 1-Na, 1-K, or 1-Ca) can exist in the form of a pharmaceutically acceptable solvate. In some embodiments, the compounds described herein (e.g., Compound 1, 1-Na, 1-K, or 1-Ca) can exist in a hydrate form. In some embodiments, the compounds described herein (e.g., Compound 1, 1-Na, 1-K, or 1-Ca) can exist in an anhydrous form.

Pharmaceutical Compositions

In some embodiments, the present invention provides a pharmaceutical composition comprising one or more of the compounds described herein (e.g., Compound 1, 1-Na, 1-K, or 1-Ca). Typically, the pharmaceutical composition comprises a therapeutically effective amount of one or more of the compounds described herein (e.g., Compound 1, 1-Na, 1-K, or 1-Ca) and optionally a pharmaceutically acceptable excipient or carrier. In some embodiments, the pharmaceutical composition comprises one or more of the substantially pure Compound 1, 1-Na, 1-K, and 1-Ca as described herein. In some embodiments, the pharmaceutical composition comprises one or more of the crystalline forms selected from Form I of Compound 1, Form II of Compound 1-Na, Form III of Compound 1-K, and Form IV of Compound 1-Ca. The pharmaceutical composition can be formulated for any routes of administration, for example, oral administration.

Certain specific embodiments of the present invention are directed to a pharmaceutical composition comprising a therapeutically effective amount of Compound 1-Na and optionally a pharmaceutically acceptable excipient or carrier. In some embodiments, the pharmaceutical composition comprising Compound 1-Na can be formulated for oral, parenteral, nasal, pulmonary, buccal, topical or transdermal administration. For example, in some embodiments, the pharmaceutical composition comprising Compound 1-Na can be an oral formulation, such as a capsule, tablet, or aqueous solution. In some embodiments, the pharmaceutical composition comprises the substantially pure Compound 1-Na as described herein. In some embodiments, the Compound 1-Na exists in Form II. In some embodiments, the pharmaceutical composition is free or substantially free of Compound 1-Na in any solid form other than Form II. For example, in some embodiments, there is no XRPD detectable solid form of Compound 1-Na other than Form II in the pharmaceutical composition.

The pharmaceutical composition comprising Compound 1-Na is typically storage stable. For example, in one example, when tested for stability by storing at 40° C. at a relative humidity of 75% for up to 6 months or more (e.g., 1, 2, 3, 4, 5, or 6 months), the pharmaceutical composition (a) contains substantially the same amount of Compound 1-Na as determined by HPLC, (b) with no increased amount of impurities or degradants as determined by HPLC, and/or (c) has essentially the same dissolution profile as determined by the dissolution methods described herein.

The pharmaceutical composition comprising Compound 1-Na can also be characterized by an in vitro dissolution profile. In some embodiments, the pharmaceutical composition can be formulated as a solid dosage form, such as a capsule or tablet. In some embodiments, the solid dosage form can be formulated as an immediate release formulation, for example, releasing at least 70% (e.g., at least 80%, at least 85%, at least 90%, or essentially all) of the Compound 1-Na within 45 minutes, when tested using USP II Paddle in a dissolution medium (900 mL) having a pH of about 6.8 (using monobasic sodium phosphate buffer) at a paddle speed of 50 rpm.

Typically, the pharmaceutical composition comprising Compound 1-Na is formulated as a solid dosage form. In some embodiments, the solid dosage form is an oral solid dosage form. In some embodiments, the solid dosage form is a capsule or tablet. In some embodiments, the capsule or tablet is enteric coated. In some embodiments, the capsule or tablet is non-enteric coated. In any of the embodiments described herein, the pharmaceutical composition can be non-enteric coated.

The pharmaceutical composition herein can include Compound 1-Na in various amounts, for example, in an amount effective for treating the diseases or disorders described herein, such as gout or hyperuricemia. Other suitable amounts are described herein.

In some embodiments, the active ingredient in the pharmaceutical composition can consist essentially of Compound 1-Na. For example, the pharmaceutical composition herein can include Compound 1-Na along with its free acid form as the only active ingredient. Although Compound 1-Na is a sodium salt, those skilled in the art would understand that certain free acid form may be present in the pharmaceutical composition, e.g., through equilibrium. In some embodiments, the pharmaceutical composition includes Compound 1-Na along with its free acid form as the only active ingredient. Typically, the pharmaceutical composition is substantially free of Compound 1, for example, with an amount less than 5% by weight (e.g., less than 3%, less than 1%, less than 0.2%, less than 0.1%, less than 0.05%, or non-detectable). In some embodiments, the pharmaceutical composition is also substantially free of other salts of Compound 1, for example, with an amount less than 5% by weight (e.g., less than 3%, less than 1%, less than 0.2%, less than 0.1%, less than 0.05%, or non-detectable). However, in some embodiments, the pharmaceutical composition herein can also include other active ingredients, for example, other compounds described herein or other active ingredients useful for treating the diseases or disorders described herein, such as gout or hyperuricemia.

In some embodiments, the pharmaceutical composition comprises a second agent. In some embodiments, the second agent is a xanthine oxidase inhibitor, a xanthine dehydrogenase inhibitor, a xanthine oxidoreductase inhibitor, or a combination thereof. In some embodiments, the second agent is allopurinol, febuxostat or a combination thereof. In some embodiments, the second agent is included in the pharmaceutical composition in an amount effective for treating gout or hyperuricemia.

In some embodiments, the second agent and the compounds described herein (e.g., Compound 1-Na) are formulated in a single dosage form, such as a single tablet or single capsule. In some embodiments, a kit is provided which includes a unit dosage form comprising one or more of the compounds described herein (e.g., Compound 1-Na) and a separate unit dosage form comprising the second agent. The amounts of the compounds described herein (e.g., Compound 1-Na) and second agent can vary, so long as the combined administration (e.g., concurrently or sequentially) is therapeutically effective, for example, in treating gout or hyperuricemia.

Various excipients or carriers can be included in the pharmaceutical compositions described herein. Typically, the pharmaceutical composition herein can include one or more excipients or carriers selected from filling agents (such as lactose, microcrystalline cellulose, mannitol, etc.), disintegrants (e.g., croscarmellose sodium), glidants (e.g., colloidal silicon dioxide), lubricants (e.g., sodium stearyl fumarate), antioxidants, stabilizers, preservatives, diluents, solvents, sweetening agents, viscosity-increasing agents, chelating agents, surfactants, flavorings, coating agents, gelling agents, binders and release modifiers. Those skilled in the art would know that other excipients/carriers can also be used and know how to choose appropriate excipients/carriers when formulating the compounds herein according to the intended uses. In some specific embodiments, the pharmaceutical composition includes one or more (e.g., 1, 2, 3, 4, 5, 6, or 7) of the following: lactose, microcrystalline cellulose, mannitol, croscarmellose sodium, colloidal silicon dioxide, and sodium stearyl fumarate. Any suitable amount of such excipients and carriers can be used. The amount of excipients and/or carriers can also be adjusted, for example, to achieve a desired immediate release dissolution profile described herein. In some embodiments, the excipients and carriers are used in an amount at or below the upper limit of the respective excipient or carrier that the U.S. Food and Drug Administration, or other corresponding competent agencies, has determined to be safe for human use. Additional suitable examples of excipients or carriers can be found in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), the contents of which are incorporated herein by reference in their entirety.

Other compounds described herein, for example, any one or more of Compounds 1, 1-K, and 1-Ca, can be formulated similarly to those described herein for Compound 1-Na. For example, such compounds can also be formulated in a solid dosage form (e.g., enteric coated tablet or capsule or non-enteric coated tablet or capsule).

For example, Compound 1-K can be included in any of the pharmaceutical compositions described herein where Compound 1-Na is indicated as suitable. In some embodiments, Compound 1-K can substitute Compound 1-Na as the active ingredient in any of the pharmaceutical compositions described herein where Compound 1-Na is indicated as suitable. In some embodiments, Form III of Compound 1-K is included in the pharmaceutical composition. In some embodiments, Compound 1-K in the pharmaceutical composition is in Form III and is substantially free from other solid state forms.

In some embodiments, Compound 1 can be included in any of the pharmaceutical compositions where Compound 1-Na is indicated as suitable. In some embodiments, Compound 1 can substitute Compound 1-Na as the active ingredient in any of the pharmaceutical compositions described herein where Compound 1-Na is indicated as suitable. In some embodiments, Form I of Compound 1 is included in the pharmaceutical composition. In some embodiments, Compound 1 in the pharmaceutical composition is in Form I and is substantially free from other solid state forms.

In some embodiments, Compound 1-Ca can be included in any of the pharmaceutical compositions where Compound 1-Na is indicated as suitable. In some embodiments, Compound 1-Ca can substitute Compound 1-Na as the active ingredient in any of the pharmaceutical compositions described herein where Compound 1-Na is indicated as suitable. In some embodiments, Form IV of Compound 1-Ca is included in the pharmaceutical composition. In some embodiments, Compound 1-Ca in the pharmaceutical composition is in Form IV and is substantially free from other solid state forms.

Methods of Treatment

The compounds and pharmaceutical compositions described herein can be used for treating various diseases and disorders. As shown in U.S. Pat. No. 9,809,580, carboxylic acid compounds such as Compound 1 are effective inhibitors of URAT-1 and are useful in treating various diseases and disorders that are mediated by abnormal levels of uric acid.

In some embodiments, a method of treating a disease or disorder in a subject in need thereof is provided. In some embodiments, the disease or disorder is mediated by abnormal levels of uric acid. In some embodiments, inhibition of URAT-1 is beneficial for the treatment of the disease or disorder. In some embodiments, the disease or disorder is one or more selected from gout, gouty arthritis, a recurrent gout attack, hyperuricemia, joint inflammation, arthritis, urolithiasis, kidney disease, kidney stones, kidney failure, hypertension, cardiovascular disease, coronary heart disease, Lesch-Nyhan syndrome, Kelley-Seegmiller syndrome, plumbism, hyperparathyroidism, psoriasis and sarcoidosis. In some embodiments, the disease or disorder is gout. In some embodiments, the disease or disorder is hyperuricemia.

In some embodiment, a method of lowering blood level of uric acid in a subject in need thereof is provided.

In some embodiment, a method of promoting excretion of uric acid in a subject in need thereof is provided.

Typically, the methods described herein include administering to the subject a therapeutically effective amount of one or more of the compounds described herein (e.g., Compound 1, 1-Na, 1-K, or 1-Ca) or the pharmaceutical compositions described herein (e.g., those including Compound 1-Na or 1-K). The compounds and pharmaceutical compositions can be administered to the subject via any routes of administration. For example, in some embodiments, the compounds and pharmaceutical compositions can be administered to the subject orally.

In some specific embodiments, the method is for treating gout. In some embodiments, the method comprises orally administering to the subject a therapeutically effective amount of Compound 1-Na, e.g., any of the substantially pure Compound 1-Na as described herein. In some embodiments, the method comprises orally administering to the subject a therapeutically effective amount of any of the pharmaceutical composition described herein that includes Compound 1-Na. In some embodiments, the Compound 1-Na can exist in Form II. In some embodiments, the pharmaceutical composition comprises Form II of Compound 1-Na and is substantially free of any other form of Compound 1-Na, e.g., non-detectable by XRPD. In some embodiments, the active ingredient of the pharmaceutical composition consists essentially of Compound 1-Na. However, in some embodiments, the method can further comprise administering to the subject a second agent as described herein, such as a xanthine oxidase inhibitor, a xanthine dehydrogenase inhibitor, a xanthine oxidoreductase inhibitor, or a combination thereof. In some embodiments, the second agent can be allopurinol, febuxostat or a combination thereof. In some embodiments, the second agent can be administered to the subject concurrently (e.g., in a single dosage form) or sequentially (e.g., in separate dosage forms) to the subject. The amounts of the compounds described herein (e.g., Compound 1-Na) and second agent can vary, so long as the combined administration (e.g., concurrently or sequentially) is therapeutically effective, for example, for treating gout or hyperuricemia.

Definitions

As used herein, the term "about" modifying an amount related to the invention refers to variation in the numerical quantity that can occur, for example, through routine testing and handling; through inadvertent error in such testing and handling; through differences in the manufacture, source, or purity of ingredients employed in the invention; and the like.

As used herein, "about" a specific value also includes the specific value, for example, about 10% includes 10%. Whether or not modified by the term "about", the claims include equivalents of the recited quantities. In one embodiment, the term "about" means within 20% of the reported numerical value.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound described herein to a subject in need of such treatment.

The term "therapeutically effective amount," as used herein, refers to that amount of a therapeutic agent (e.g., any one or more of the compounds described herein) sufficient to result in amelioration of one or more symptoms of a disorder or condition (e.g., gout, hyperuricemia), or prevent appearance or advancement of a disorder or condition, or cause regression of or cure from the disorder or condition.

The term "subject" (alternatively referred to herein as "patient") as used herein, refers to an animal, preferably a mammal, most preferably a human, who has been the object of treatment, observation or experiment. In any of the embodiments described herein, the subject can be a human.

ALTERNATIVE EMBODIMENTS

Embodiment 1. A crystalline form of Compound 1, Compound 1-Na, Compound 1-K, or Compound 1-Ca.

Embodiment 2. The crystalline form of embodiment 1, which is a crystalline form I of Compound 1, wherein the crystalline form is characterized by an XRPD pattern having one or more (e.g., 1, 2, 3, 4, 5, 6, 7, 8, or all) of the following peaks: 7.0, 10.2, 10.6, 14.0, 20.4, 21.9, 23.4, 24.9, and 25.9 degrees 2 theta, ±0.2°.

Embodiment 3. The crystalline form of embodiment 2, wherein the crystalline form is characterized by an XRPD pattern having four or more (e.g., 4, 5, 6, 7, 8, or all) of the following peaks: 7.0, 10.2, 10.6, 14.0, 20.4, 21.9, 23.4, 24.9, and 25.9 degrees 2 theta, ±0.2°.

Embodiment 4. The crystalline form of embodiment 2, wherein the crystalline form is characterized by an XRPD pattern having six or more of the following peaks: 7.0, 10.2, 10.6, 14.0, 20.4, 21.9, 23.4, 24.9, and 25.9 degrees 2 theta, ±0.2°.

Embodiment 5. The crystalline form of embodiment 2, wherein the crystalline form is characterized by an XRPD pattern substantially the same as shown in FIG. 1A.

Embodiment 6. The crystalline form of any one of embodiments 2-5, wherein the crystalline form is characterized (1) a Differential Scanning calorimetry (DSC) pattern having an endotherm peak with peak temperature at about 175.9° C.; (2) a Differential Scanning calorimetry (DSC) pattern substantially the same as shown in FIG. 1B; or a combination thereof.

Embodiment 7. The crystalline form of embodiment 1, which is a crystalline form II of Compound 1-Na, characterized by an X-ray powder diffraction (XRPD) pattern having one or more of the following peaks: 8.8, 15.2, 16.2, 17.2, 17.6, 18.6, 20.2, 20.9, 21.7, 22.2, 23.1, 25.2, 25.9, and 26.4 degrees 2 theta, ±0.2°.

Embodiment 8. The crystalline form of embodiment 7, characterized by an XRPD pattern having four or more of the following peaks: 8.8, 15.2, 16.2, 17.2, 17.6, 18.6, 20.2, 20.9, 21.7, 22.2, 23.1, 25.2, 25.9, and 26.4 degrees 2 theta, ±0.2°.

Embodiment 9. The crystalline form of embodiment 7, characterized by an XRPD pattern having eight or more of the following peaks: 8.8, 15.2, 16.2, 17.2, 17.6, 18.6, 20.2, 20.9, 21.7, 22.2, 23.1, 25.2, 25.9, and 26.4 degrees 2 theta, ±0.2°.

Embodiment 10. The crystalline form of embodiment 7, characterized by an XRPD pattern substantially the same as shown in FIG. 2A.

Embodiment 11. The crystalline form of any one of embodiments 7-10, characterized by (1) a Differential Scanning calorimetry (DSC) pattern having an endotherm peak with peak temperature at about 301.3° C.; (2) a Differential Scanning calorimetry (DSC) pattern substantially the same as shown in FIG. 2B, or a combination thereof.

Embodiment 12. The crystalline form of embodiment 1, which is Form III of Compound 1-K, wherein the crystalline form is characterized by an XRPD pattern having one or more (e.g., 1, 2, 3, 4, 5, 6, 7, 8, 9, 10, or all) of the following peaks: 8.3, 14.5, 14.8, 15.6, 16.7, 17.0, 18.2, 19.6, 20.2, 22.2, 22.6, and 25.1 degrees 2 theta, ±0.2°.

Embodiment 13. The crystalline form of embodiment 12, wherein the crystalline form is characterized by an XRPD pattern having four or more (e.g., 4, 5, 6, 7, 8, 9, 10, or all) of the following peaks: 8.3, 14.5, 14.8, 15.6, 16.7, 17.0, 18.2, 19.6, 20.2, 22.2, 22.6, and 25.1 degrees 2 theta, ±0.2°.

Embodiment 14. The crystalline form of embodiment 12, wherein the crystalline form is characterized by an XRPD pattern having eight or more (e.g., 8, 9, 10, or all) of the following peaks: 8.3, 14.5, 14.8, 15.6, 16.7, 17.0, 18.2, 19.6, 20.2, 22.2, 22.6, and 25.1 degrees 2 theta, ±0.2°.

Embodiment 15. The crystalline form of embodiment 12, wherein the crystalline form is characterized by an XRPD pattern substantially the same as shown in FIG. 3A.

Embodiment 16. The crystalline form of any one of embodiments 12-15, wherein the crystalline form is characterized by (1) a Differential Scanning calorimetry (DSC) pattern having an endotherm peak with peak temperature at about 299.9° C.; (2) a Differential Scanning calorimetry (DSC) pattern substantially the same as shown in FIG. 3B, or a combination thereof.

Embodiment 17. The crystalline form of embodiment 1, which is a crystalline form of Form IV of Compound 1-Ca, wherein the crystalline form is characterized by an XRPD pattern having one or more (e.g., 1, 2, 3, 4, 5, 6, 7, 8, 9, 10, 11, 12, 13, or all) of the following peaks: 4.4, 6.5, 9.1, 12.3, 13.0, 13.4, 13.7, 14.5, 16.0, 16.8, 18.2, 19.8, 21.0, and 21.6 degrees 2 theta, ±0.2°.

Embodiment 18. The crystalline form of embodiment 17, wherein the crystalline form is characterized by an XRPD pattern having four or more (e.g., 4, 5, 6, 7, 8, 9, 10, 11, 12, 13, or all) of the following peaks: 4.4, 6.5, 9.1, 12.3, 13.0, 13.4, 13.7, 14.5, 16.0, 16.8, 18.2, 19.8, 21.0, and 21.6 degrees 2 theta, ±0.2°.

Embodiment 19. The crystalline form of embodiment 17, wherein the crystalline form is characterized by an XRPD pattern having eight or more (e.g., 8, 9, 10, 11, 12, 13, or all)

of the following peaks: 4.4, 6.5, 9.1, 12.3, 13.0, 13.4, 13.7, 14.5, 16.0, 16.8, 18.2, 19.8, 21.0, and 21.6 degrees 2 theta, +0.2°.

Embodiment 20. The crystalline form of embodiment 17, wherein the crystalline form is characterized by an XRPD pattern substantially the same as shown in FIG. 4A.

Embodiment 21. The crystalline form of any one of embodiments 17-20, wherein the crystalline form is characterized by (1) a Differential Scanning calorimetry (DSC) pattern having an endotherm peak with peak temperature at about 145.1° C.; (2) a Differential Scanning calorimetry (DSC) pattern substantially the same as shown in FIG. 4B, or a combination thereof.

Embodiment 22. A substantially pure compound selected from (1) a substantially pure Compound 1 comprising the crystalline form of any one of embodiments 2-6; (2) a substantially pure Compound 1-Na comprising the crystalline form of any one of embodiments 7-11; (3) a substantially pure Compound 1-K comprising the crystalline form of any one of embodiments 12-16; and (4) a substantially pure Compound 1 comprising the crystalline form of any one of embodiments 17-21.

Embodiment 23. A pharmaceutical composition comprising any one or more of the crystalline form of embodiments 1-21 or the substantially pure compound of embodiment 22 and optionally a pharmaceutically acceptable excipient or carrier.

Embodiment 24. The pharmaceutical composition of embodiment 23, which comprises Form I of Compound 1 according to any of embodiments 2-6 and is substantially free (e.g., not detectable by XRPD) of other solid forms of Compound 1 or a pharmaceutically acceptable salt thereof.

Embodiment 25. The pharmaceutical composition of embodiment 23, which comprises Form II of Compound 1-Na according to any of embodiments 7-11 and is substantially free (e.g., not detectable by XRPD) of other solid forms of Compound 1-Na.

Embodiment 26. The pharmaceutical composition of embodiments 25, which is substantially free of Compound 1, a non-sodium salt thereof, or a combination thereof.

Embodiment 27. The pharmaceutical composition of embodiments 23, which comprises Form III of Compound 1-K according to any of embodiments 12-16 and is substantially free (e.g., not detectable by XRPD) of other solid forms of Compound 1-K.

Embodiment 28. The pharmaceutical composition of embodiments 27, which is substantially free of Compound 1, a non-potassium salt thereof, or a combination thereof.

Embodiment 29. The pharmaceutical composition of embodiment 23, which comprises Form IV of Compound 1-Ca according to any of embodiments 17-21 and is substantially free (e.g., not detectable by XRPD) of other solid forms of Compound 1-Ca.

Embodiment 30. The pharmaceutical composition of embodiments 29, which is substantially free of Compound 1, a non-calcium salt thereof, or a combination thereof.

Embodiment 31. The pharmaceutical composition of any one of embodiments 23-30, which is not enteric coated.

Embodiment 32. The pharmaceutical composition of any one of embodiments 23-30, which is enteric coated.

Embodiment 33. The pharmaceutical composition of any one of embodiments 23-32, which is in the form of a tablet or capsule.

Embodiment 34. The pharmaceutical composition of any one of embodiments 23-33, wherein the active ingredient of the pharmaceutical composition consisting essentially of Compound 1, Compound 1-Na, Compound 1-K, or Compound 1-Ca.

Embodiment 35. A method of treating one or more diseases or disorders chosen from gout, gouty arthritis, recurrent gout attack, hyperuricemia, joint inflammation, arthritis, urolithiasis, kidney disease, kidney stone, kidney failure, hypertension, cardiovascular disease, coronary heart disease, Lesch-Nyhan syndrome, Kelley-Seegmiller syndrome, plumbism, hyperparathyroidism, psoriasis and sarcoidosis, the method comprising administering to a subject in need thereof a therapeutically effective amount of the crystalline form of any one of embodiments 1-21 or the substantially pure compound of embodiment 22 or the pharmaceutical composition of any one of embodiments 23-34.

Embodiment 36. A method of treating hyperuricemia, comprising administering to a subject in need thereof a therapeutically effective amount of the crystalline form of any one of embodiments 1-21 or the substantially pure compound of embodiment 22 or the pharmaceutical composition of any one of embodiments 23-34.

Embodiment 37. A method of treating gout, comprising administering to a subject in need thereof a therapeutically effective amount of the crystalline form of any one of embodiments 1-21 or the substantially pure compound of embodiment 22 or the pharmaceutical composition of any one of embodiments 23-34.

Embodiment 38. The method of embodiment 37, further comprising administering to the subject a second agent effective for treating gout.

Embodiment 39. The method of embodiment 38, wherein the second agent is a xanthine oxidase inhibitor, a xanthine dehydrogenase inhibitor, a xanthine oxidoreductase inhibitor, or a combination thereof.

Embodiment 40. The method of embodiment 38, wherein the second agent is allopurinol, febuxostat or a combination thereof.

Embodiment 41. A method of lowering blood levels of uric acid, comprising administering to a subject in need thereof an effective amount of the crystalline form of any one of embodiments 1-21 or the substantially pure compound of embodiment 22 or the pharmaceutical composition of any one of embodiments 23-34.

Embodiment 42. A method of promoting excretion of uric acid, comprising administering to a subject in need thereof an effective amount of the crystalline form of any one of embodiments 1-21 or the substantially pure compound of embodiment 22 or the pharmaceutical composition of any one of embodiments 23-34.

Embodiment 43. The method of any one of embodiments 35-42, wherein the crystalline form or pharmaceutical composition is administered to the subject orally.

EXAMPLES

Example 1. General Methods

Materials: the starting materials, reagents, solvents, etc. are generally available through commercial sources.

POWDER X-RAY DIFFRACTION (XRPD): The solid samples were examined using X-ray diffractometer (Bruker D8 advance). The system is equipped with LynxEye detector. The x-ray wavelength is 1.5406 Å. The samples were scanned from 3 to 40° 2θ, at a step size 0.02° 2θ. The tube voltage and current were 40 KV and 40 mA, respectively.

The sample was transferred from sample container onto zero background XRPD-holder and grounded gently.

TGA ANALYSIS: TGA analysis was carried out on a TA Instruments TGA Q500. Samples was placed in a tarred platinum or aluminum pan, automatically weighed, and inserted into the TGA furnace. The samples were heated at a rate of 10° C./min to a final temperature. The purge gas is nitrogen for balance at 40 mL/min and for the sample at 60 mL/min, respectively.

DSC ANALYSIS: DSC analysis was conducted on a TA Instruments Q200. The calibration standard was indium. A sample in weight was placed into a TA DSC pan, and weight was accurately recorded. Crimped pans were used for analysis and the samples were heated under nitrogen (50 mL/min) at a rate of 10° C./min, up to a final temperature.

DYNAMIC MOISTURE SORPTION: Dynamic moisture adsorption and desorption were studied using IGA sorp (Hiden Isochema Ltd. Warrington, UK). About 3-5 mg of prepared sample was placed in a sample basket and hung in the measuring chamber of an IGA Sorp. For an isotherm test, the chamber temperature is maintained by a water bath at constant 25±1° C. The sample was tested at a targeted RH of 10 to 90% full cycle in step mode. The analysis was performed in 10% RH increments. Time duration at each RH was set as min.30 minutes to max. 120 min, so that the sample could reach equilibrium with the chamber environment. Data was collected in 3 minutes increment.

HPLC ANALYSIS: a representative HPLC method is shown below, which can be used, for example, to analyze the purity of the compounds herein.

Instrument: Agilent 1260 Series

Flow rate: 1.2 mL/min

Mobile phase: A: 0.1% TFA in water

B: 0.1% TFA in MeOH

Injection volume: 2 μL

Column: Agilent Eclipse plus C18, 3.5 um, 4.6*100 mm

Column Temperature: 40° C.

Detection: 255 nm

Run Time: 8 minutes (2 minutes delay for next injection)

Gradient (T/B %): 0.0/30, 6.0/70 and 8.0/90

Example 2. Preparation of 2-(1-(((3-(4-cyanophenyl)pyridin-4-yl)thio)methyl)cyclopropyl)acetic acid

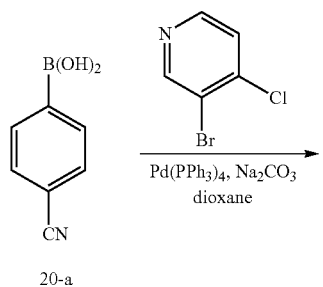

20-a

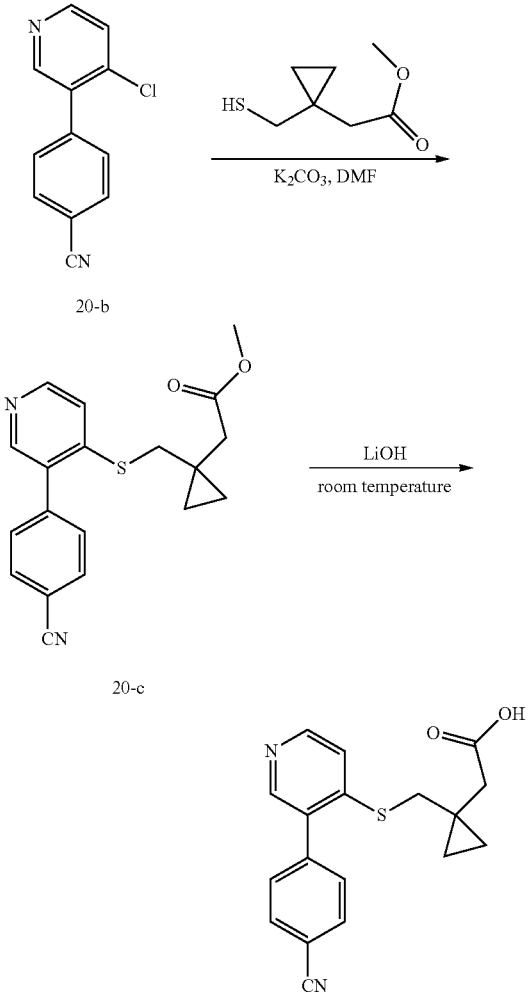

Step 1: Synthesis of 4-(4-chloropyridin-3-yl)benzonitrile (20-b)

Under $N_2$ atmosphere, 1,4-dioxane (10 v), 3-bromo-4-chloropyridine (1400.0 g, 1.0 eq), 4-cyanophenylboronic acid (1.02 eq), $Na_2CO_3$ (2 M aq, 2.0 eq) and KOAc (1.0 eq) were charged into a reactor. Inert the reactor with nitrogen and then $Pd(PPh_3)_4$ (0.02 wt) was added. The resulting mixture was heated at 90±5° C. for 24 hours until the content of 3-bromo-4-chloropyridine was NMT 5.0%. The reaction mixture was cooled to 20±5° C., filtered and washed the cake with 1,4-dioxane (2 v). The combined filtrate was concentrated to 10 v under reduced pressure, and then added $H_2O$ (20 v) which resulted in the formation of white solid. The mixture was filtered and the filter cake was washed with $H_2O$ (2 v). The cake was dissolved in DCM (5 v), and the resulting mixture was separated to remove residual water. 3-Mercaptopropyl ethyl sulfide Silica (0.15 wt) was added, and the mixture was filtered and washed with DCM (2 v). 3-Mercaptopropyl ethyl sulfide Silica (0.15 wt) was added to the combined filtrate again, and the mixture was filtered and washed with DCM (2 v). The resulting filtrate was concentrated to 2-3 v and purified water (8 v) was added. The mixture was stirred for at least 30 minutes and filtered. The filter cake was washed with water (2 v), and dried in a vacuum oven at 50±5° C. to give the crude product as a white solid (Purity: 90.4%), which was used for next reaction without further purification.

Step 2: Synthesis of methyl 2-(1-(((3-(4-cyanophenyl)pyridin-4-yl)thio) methyl)cyclopropyl)acetate (20-c)

Under $N_2$ atmosphere, DMF (6 v) was charged into a reactor, and then compound 20-b (1313.6 g, 1.0 eq), methyl 2-(1-(mercaptomethyl)cyclopropyl)acetate (1.05 eq) and $K_2CO_3$ (1.2 eq) were added. The resulting mixture was heated at 80±5° C. for 3 hours until the content of compound 20-b was NMT 1.0%. The reaction mixture was cooled to 20±5° C., filtered and washed the cake with EA (2 v). The combined filtrate was added $H_2O$ (10 v), and extracted with EA (5 v). The combined organic layers were washed with saturated aq. $NaHCO_3$ and NaCl solution. The resulting organic phase was concentrated to 2-3 v under reduced pressure, and n-heptane (10 v) was added. The resulting mixture was filtered and washed with n-heptane (2 v). The filter cake was dissolved in EA (10 v), and the resulting organic phase was concentrated to 2-3 v under reduced pressure at 50±5° C. (water temperature). n-Heptane (10 v) was added to the mixture, and the solid was collected by filtration and washed with n-heptane (2 v) after being stirred for one hour at 40±5° C. The filter cake was dissolved in MTBE (10 v) at 50±5° C., and 3-mercaptopropyl ethyl sulfide Silica (0.20 wt) was added. The resulting mixture was stirred for at least 5 hours at 50±5° C., filtered and washed with MTBE (2 v). 3-Mercaptopropyl ethyl sulfide Silica (0.20 wt) was again added to the combined filtrate, stirred for at least 5 hours at 50±5° C., and filtered. The filter cake was washed with MTBE (2 v) and the combined organic phase was concentrated to 2-3 v under reduced pressure. n-Heptane (10 v) was added to the mixture, and the solid was collected by filtration. The filter cake was dried in a vacuum oven at 50±5° C. to give the crude compound 20-c as a white solid (Purity: 95.2%).

Synthesis of 2-(1-(((3-(4-cyanophenyl)pyridin-4-yl)thio)methyl) cyclopropyl)acetic acid (1)

To a stirred solution of compound 20-c (1533.0 g, 1.0 eq) in THF (10 v) was added an aqueous solution of LiOH (1.1 eq, 2 M) under $N_2$ atmosphere. The resulting mixture was stirred at 25±3° C. for 2 hours until the content of compound 20-c was NMT 1.0%. After the reaction mixture was quenched with $H_2O$ (10 v), it was extracted with MTBE. The aqueous phase was cooled to 0±5° C. and a 20% of aqueous HOAc solution was added slowly at 0±5° C. to adjust the pH to 5.0-6.0. The resultant solid was collected by filtration, washed with $H_2O$ (5 v) and dried to give Form I of Compound 1 as an off-white solid, which was characterized by XRPD (Purity: 99.6%). HNMR (300 MHz, DMSO-$d_6$, ppm): δ 12.17 (bs, 1H), 8.43 (d, J=5.4 Hz, 1H), 8.27 (s, 1H), 7.97 (d, J=8.4 Hz, 2H), 7.65 (d, J=8.4 Hz, 2H), 7.42 (d, J=5.4 Hz, 1H), 3.18 (s, 2H), 2.25 (s, 2H), 0.49-0.59 (m, 4H).

TABLE 1

XRPD Diffraction Angles of Crystalline Form I of Compound 1

| Angle 2-Theta/° | Intensity % |
| --- | --- |
| 6.964 | 40.1 |
| 10.158 | 11.5 |

TABLE 1-continued

XRPD Diffraction Angles of Crystalline Form I of Compound 1

| Angle 2-Theta/° | Intensity % |
| --- | --- |
| 10.582 | 5.4 |
| 12.608 | 0.8 |
| 13.966 | 100 |
| 14.641 | 1.6 |
| 15.677 | 2 |
| 18.386 | 2.5 |
| 19.3 | 1.5 |
| 19.602 | 6.8 |
| 19.86 | 5 |
| 20.405 | 31.4 |
| 21.028 | 2.4 |
| 21.26 | 1.6 |
| 21.549 | 1.6 |
| 21.859 | 8 |
| 22.941 | 3.6 |
| 23.426 | 16.1 |
| 23.719 | 3.4 |
| 24.041 | 0.9 |
| 24.894 | 7.5 |
| 25.709 | 4.8 |
| 25.933 | 11.1 |
| 26.337 | 1.1 |
| 26.715 | 3.8 |
| 27.094 | 2.6 |
| 28.074 | 2.6 |
| 28.832 | 1 |
| 29.597 | 5.7 |
| 30.042 | 5.7 |
| 30.317 | 1.6 |
| 30.814 | 3.5 |
| 31.245 | 1.3 |
| 31.737 | 1.2 |
| 32.116 | 1.1 |
| 32.371 | 1.3 |
| 32.705 | 2.5 |
| 33.112 | 0.9 |
| 33.599 | 0.9 |
| 34.002 | 0.7 |
| 35.006 | 0.7 |
| 35.582 | 1.6 |
| 36.421 | 1.1 |
| 36.661 | 1.2 |
| 36.949 | 1.1 |
| 37.572 | 1.7 |
| 37.894 | 0.7 |
| 38.719 | 1.6 |
| 39.686 | 1.6 |

Example 3. Preparation of Sodium 2-(1-(((3-(4-cyanophenyl)pyridin-4-yl)thio)methyl)cyclopropyl) acetate 2-(1-(((3-(4-cyanophenyl)pyridin-4-yl)thio)methyl)cyclopropyl)acetic acid (2.003 g) was added into a glass flask. THF (80 mL) was then added to form a clear solution. NaOH (264.2 mg) was then added into the flask, and the mixture was stirred for 4 hours until yellow precipitation appeared. The sodium salt solid was filtered, washed with THF and dried under vacuum. HNMR (400 MHz, DMSO-$d_6$, ppm): δ 8.40 (d, J=5.6 Hz, 1H), 8.22 (s, 1H), 7.96 (d, J=8.4 Hz, 2H), 7.65 (d, J=8.4 Hz, 2H), 7.63 (d, J=5.6 Hz, 1H), 3.34 (s, 2H), 1.89 (s, 2H), 0.34-0.42 (m, 4H).

The obtained solid was analyzed. A representative XRPD spectrum was shown in FIG. 2A and a representative DSC spectrum was shown in FIG. 2B. The sodium salt was determined to be anhydrous, with an onset melting point of about 297.2° C.

TABLE 2

XRPD Diffraction Angles of Crystalline Form II of Compound 1-Na

| Angle 2-Theta/° | Intensity % |
|---|---|
| 4.03 | 12 |
| 5.521 | 7.6 |
| 8.421 | 9 |
| 8.803 | 20.2 |
| 14.275 | 7.9 |
| 15.241 | 65.6 |
| 16.235 | 69.8 |
| 16.796 | 6.9 |
| 17.196 | 43.2 |
| 17.592 | 17.2 |
| 18.576 | 27 |
| 20.197 | 100 |
| 20.895 | 32.3 |
| 21.666 | 30.9 |
| 22.227 | 67.1 |
| 23.089 | 34.6 |
| 23.912 | 4.8 |
| 25.247 | 27.2 |
| 25.88 | 52.1 |
| 26.354 | 30.8 |
| 26.75 | 10.3 |
| 27.139 | 17.1 |
| 27.866 | 6.8 |
| 28.466 | 7 |
| 28.805 | 21.5 |
| 29.248 | 17.1 |
| 29.803 | 17.4 |
| 30.363 | 10.7 |
| 31.156 | 5.4 |
| 31.669 | 11.8 |
| 31.957 | 11.9 |
| 32.629 | 5.6 |
| 33.003 | 6.2 |
| 33.25 | 5.9 |
| 33.862 | 12.8 |
| 34.731 | 26.4 |
| 35.551 | 6.3 |
| 36.018 | 5.4 |
| 36.687 | 7.7 |
| 37.241 | 5.9 |
| 37.552 | 6.1 |
| 38.267 | 10.5 |
| 38.905 | 3.9 |
| 39.214 | 5.3 |
| 39.616 | 5.3 |

TABLE 3

XRPD Diffraction Angles of Crystalline Form III of Compound 1-K

| Angle 2-Theta/° | Intensity % |
|---|---|
| 4.038 | 48.1 |
| 8.332 | 43.8 |
| 13.758 | 9 |
| 14.522 | 15.8 |
| 14.774 | 29.7 |
| 15.625 | 24 |
| 16.681 | 19.7 |
| 16.973 | 26.6 |
| 18.151 | 20.3 |
| 19.614 | 55 |
| 20.224 | 21.1 |
| 21.265 | 15.5 |
| 21.473 | 15 |
| 22.199 | 62.8 |
| 22.556 | 33.2 |
| 25.138 | 100 |
| 25.515 | 23 |
| 25.919 | 20 |
| 26.28 | 11.3 |
| 27.732 | 16.3 |
| 28.41 | 12.9 |
| 28.899 | 13.6 |
| 29.321 | 19.4 |
| 30.364 | 21.8 |
| 30.984 | 12 |
| 31.487 | 7.1 |
| 32.203 | 11.3 |
| 33.167 | 8.2 |
| 33.722 | 27.8 |
| 34.252 | 9.5 |
| 34.818 | 8.9 |
| 35.716 | 7.1 |
| 36.318 | 8.3 |
| 37.05 | 9.4 |
| 38.915 | 9.5 |
| 39.543 | 12.7 |

Example 4. Preparation of Potassium 2-(1-(((3-(4-cyanophenyl)pyridin-4-yl)thio)methyl)cyclopropyl) acetate 2-(1-(((3-(4-cyanophenyl)pyridin-4-yl)thio)methyl)cyclopropyl)acetic acid (50.04 mg) was added into a vial. THF (2 mL) was then added to form a clear solution after sonication. A solution of KOH in methanol (0.1 mol/L, 1.54 mL) was then added, and the mixture was stirred for 2 hours. The solvents were evaporated to nearly dry, and 1.0 mL of ethyl acetate was added. The suspension was stirred for 30 min, and yellow precipitation appeared. The solid was filtered, collected and dried under vacuum. HNMR (400 MHz, DMSO-$d_6$, ppm): δ 8.39 (d, J=5.6 Hz, 1H), 8.22 (s, 1H), 7.96 (d, J=8.0 Hz, 2H), 7.65 (d, =8.0 Hz, 2H), 7.63 (d, J=5.6 Hz, 1H), 3.32 (s, 2H), 1.89 (s, 2H), 0.32-0.41 (m, 4H).

The obtained solid was analyzed. A representative XRPD spectrum was shown in FIG. 3A and a representative DSC spectrum was shown in FIG. 3B. The potassium salt was determined to be anhydrous, with an onset melting point of about 293.40° C.

Example 5. Preparation of Calcium 2-(1-(((3-(4-cyanophenyl)pyridin-4-yl)thio)methyl)cyclopropyl) acetate Potassium 2-(1-(((3-(4-cyanophenyl)pyridin-4-yl)thio)methyl)cyclopropyl)acetate (79.92 mg) was added into a vial, and a calcium chloride solution (12.27 mg in 1.0 mL of water) was added. The mixture was stirred for 2.5 hours, and white precipitation appeared. The calcium salt solid was obtained by filtration, and then washed with water and dried under vacuum. HNMR (300 MHz, DMSO-$d_6$, ppm): δ 8.42 (d, J=5.4 Hz, 1H), 8.23 (s, 1H), 7.96 (d, J=8.4 Hz, 2H), 7.64 (d, J=8.4 Hz, 2H), 7.55 (d, J=5.4 Hz, 1H), 3.32 (s, 2H), 1.99 (s, 2H), 0.38-0.49 (m, 4H).

The obtained solid was analyzed. A representative XRPD spectrum was shown in FIG. 4A and a representative DSC spectrum was shown in FIG. 4B. The crystalline form of the calcium salt was determined to be a hydrate. DSC showed an endothermic peak with an onset temperature of about 131.98° C., probably due to the loss of water.

Alternatively, the calcium salt can be prepared by using calcium methoxide.

TABLE 4

XRPD Diffraction Angles of Crystalline Form IV of Compound 1-Ca

| Angle 2-Theta/° | Intensity % |
|---|---|
| 3.256 | 67.1 |
| 4.44 | 100 |
| 6.449 | 93.3 |
| 9.094 | 21.2 |
| 12.256 | 25.9 |
| 12.927 | 15.5 |
| 13.385 | 23 |
| 13.745 | 15.4 |
| 14.487 | 19.3 |
| 15.175 | 14 |
| 15.962 | 15.2 |
| 16.265 | 14 |
| 16.795 | 17.2 |
| 18.193 | 21.4 |
| 19.564 | 12.1 |
| 19.776 | 16.2 |
| 20.161 | 18.5 |
| 20.974 | 29.5 |
| 21.558 | 28.7 |
| 22.63 | 9.2 |
| 23.396 | 8 |
| 24.294 | 8.1 |
| 26.343 | 14.2 |
| 27.29 | 15.4 |
| 28.344 | 11.1 |
| 31.027 | 7.7 |
| 36.86 | 6.5 |

Example 6. Properties of 2-(1-(((3-(4-cyanophenyl) pyridin-4-yl)thio)methyl)cyclopropyl)acetic acid and its salts Solubility Tests of 1-Na, 1-K, 1-Ca, and Compound 1 (Free Acid)

Weighed 5 mg of a sample solid (1-Ca salt or Compound 1) into a 8 mL of glass vial, and then added 1 mL of a pH 6.8 buffer solution or water. The suspension was centrifuged under 200 rpm at 25° C., and 0.3 mL to 0.5 mL of at 0.5 h and 2 h, respectively. At each time point, the suspension was filtered to remove solid, and the filtrate was analyzed by HPLC.

The solubilities of 1-Na and 1-K salts were very high, so the solubility was determined by visual observation. Weighed about 5 mg of sample solid (1-Na or 1-K salt) into a 2 mL of vial, and then added 5 uL of pH 6.8 buffer solution or water each time until the solids was dissolved.

The solubilities of the three salts and the Compound 1 were studied in pH 6.8 buffer and water, and the data was summarized in Table 5.

TABLE 5

Solubility (mg/mL) of salts and free acid

| Medium | 1-Na salt 0.5 h | 1-K salt 0.5 h | 1-Ca salt 0.5 h | 1-Ca salt 2 h | Compound 1 0.5 h | Compound 1 2 h |
|---|---|---|---|---|---|---|
| pH 6.8 Buffer | >400 mg/mL | >400 mg/mL | 0.264 | 0.279 | 0.083 | 0.084 |
| Water | >400 mg/mL | >400 mg/mL | 1.657 | 1.625 | 0.019 | 0.034 |

Solubility results showed that improved solubilities of the three salts over the free acid in both water and the pH 6.8 buffer. Among the three salts, solubilities of the 1-Na and the 1-K salts (>400 mg/mL) were significantly higher than that of the 1-Ca salt.

Solid Stability Tests of 1-Na, 1-K, and 1-Ca Salts

Weighed 20 mg of a salt (1-Na, or 1-K, or 1-Ca salt) into a 20 mL of glass vial and placed under an accelerated condition (40° C./75% RH). At 1- and 2-week time points, weighed 5 mg of the solid into a 10 mL of volumetric flask and added diluent (methanol:water=1:1) to dissolve, and bring to volume with diluent. HPLC and XRPD analysis were conducted at 0, 1 and 2 weeks, respectively.

All three salts were stable at 40° C./RH75% for 2 weeks. HPLC analysis showed no change in peak area.

In solid state stability testing, all three salts were physically and chemically stable at 40° C./RH75% for 2 weeks.

Solubility results showed that improved solubilities of those salts over the free acid in both water and pH 6.8 buffer. Among the three salts, the solubilities of the 1-Na and the 1-K salts (>400 mg/mL) were much higher than that of the 1-Ca salt. In addition, at 80% RH, 1-Na salt adsorbed 8.28% of water, and 1-K salt adsorbed 50.63% of water. Thus, Na salt showed advantage over potassium salt at least in terms of hygroscopicity property.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The invention claimed is:

1. A crystalline form I of Compound 1,

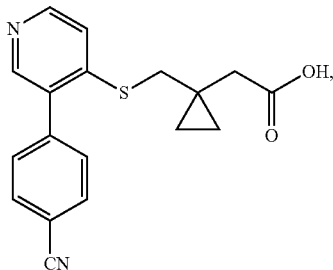

Compound 1 wherein the crystalline form I is characterized by an X-ray powder diffraction (XRPD) pattern having three or more of the following peaks: 7.0, 10.2, 10.6, 14.0, 20.4, 21.9, 23.4, 24.9, and 25.9 degrees 2 theta, ±0.2°.

2. The crystalline form I of claim 1, characterized by an XRPD pattern having the following peaks: 7.0, 10.2, 10.6, 14.0, 20.4, 21.9, 23.4, 24.9, and 25.9 degrees 2 theta, ±0.2°.

3. The crystalline form I of claim 1, characterized by an XRPD pattern substantially the same as shown in FIG. 1A.

4. A pharmaceutical composition comprising the crystalline form I of claim 1.

5. A method of treating one or more diseases or disorders chosen from gout, gouty arthritis, recurrent gout attack, hyperuricemia, joint inflammation, arthritis, urolithiasis, kidney disease, kidney stone, kidney failure, hypertension, cardiovascular disease, coronary heart disease, Lesch-Nyhan syndrome, Kelley-Seegmiller syndrome, plumbism, hyperparathyroidism, psoriasis and sarcoidosis, the method comprising administering to a subject in need thereof a therapeutically effective amount of the crystalline form I of claim 1.

6. A crystalline form III of Compound 1-K,

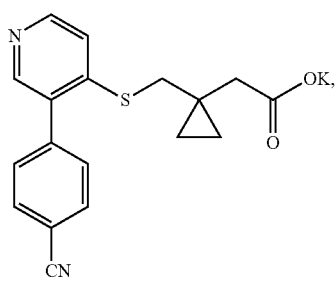

Compound 1-K wherein the crystalline form III is characterized by an X-ray powder diffraction (XRPD) pattern having three or more of the following peaks: 8.3, 14.5, 14.8, 15.6, 16.7, 17.0, 18.2, 19.6, 20.2, 22.2, 22.6, and 25.1 degrees 2 theta, ±0.2°.

7. The crystalline form III of claim 6, characterized by an XRPD pattern having the following peaks: 8.3, 14.5, 14.8, 15.6, 16.7, 17.0, 18.2, 19.6, 20.2, 22.2, 22.6, and 25.1 degrees 2 theta, ±0.2°.

8. The crystalline form of claim 6, characterized by an XRPD pattern substantially the same as shown in FIG. 3A.

9. A pharmaceutical composition comprising the crystalline form III of claim 6.

10. A method of treating one or more diseases or disorders chosen from gout, gouty arthritis, recurrent gout attack, hyperuricemia, joint inflammation, arthritis, urolithiasis, kidney disease, kidney stone, kidney failure, hypertension, cardiovascular disease, coronary heart disease, Lesch-Nyhan syndrome, Kelley-Seegmiller syndrome, plumbism, hyperparathyroidism, psoriasis and sarcoidosis, the method comprising administering to a subject in need thereof a therapeutically effective amount of the crystalline form III of claim 6.

11. A method of treating gout, comprising administering to a subject in need thereof a therapeutically effective amount of the crystalline form III of claim 6.

12. The method of claim 11, further comprising administering to the subject a second agent effective for treating gout.

13. The method of claim 12, wherein the second agent is a xanthine oxidase inhibitor, a xanthine dehydrogenase inhibitor, a xanthine oxidoreductase inhibitor, or a combination thereof.

14. The method of claim 12, wherein the second agent is allopurinol, febuxostat or a combination thereof.

15. A crystalline form IV of Compound 1-Ca,

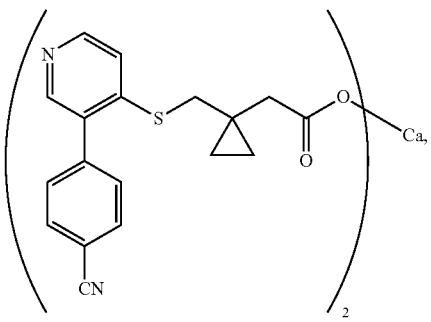

Compound 1-Ca wherein the crystalline form IV is characterized by an X-ray powder diffraction (XRPD) pattern having three or more of the following peaks: 4.4, 6.5, 9.1, 12.3, 13.0, 13.4, 13.7, 14.5, 16.0, 16.8, 18.2, 19.8, 21.0, and 21.6 degrees 2 theta, ±0.2°.

16. The crystalline form IV of claim 15, characterized by an XRPD pattern having the following peaks: 4.4, 6.5, 9.1, 12.3, 13.0, 13.4, 13.7, 14.5, 16.0, 16.8, 18.2, 19.8, 21.0, and 21.6 degrees 2 theta, ±0.2°.

17. The crystalline form IV of claim 15, wherein the crystalline form is characterized by an XRPD pattern substantially the same as shown in FIG. 4A.

18. A pharmaceutical composition comprising the crystalline form IV of claim 15.

19. A method of treating one or more diseases or disorders chosen from gout, gouty arthritis, recurrent gout attack, hyperuricemia, joint inflammation, arthritis, urolithiasis, kidney disease, kidney stone, kidney failure, hypertension, cardiovascular disease, coronary heart disease, Lesch-Nyhan syndrome, Kelley-Seegmiller syndrome, plumbism, hyperparathyroidism, psoriasis and sarcoidosis, the method comprising administering to a subject in need thereof a therapeutically effective amount of the crystalline form IV of claim 15.

* * * * *